(12) United States Patent
Prozuments et al.

(10) Patent No.: US 11,594,304 B2
(45) Date of Patent: Feb. 28, 2023

(54) IDENTIFICATION AND LOCALIZATION OF ROTATIONAL SPECTRA USING RECURRENT NEURAL NETWORKS

(71) Applicant: UCHICAGO ARGONNE, LLC, Chicago, IL (US)

(72) Inventors: Kirills Prozuments, Lagrange, IL (US); Daniel P. Zaleski, Lisle, IL (US); Prasanna Balaprakash, Chicago, IL (US)

(73) Assignee: UCHICAGO ARGONNE, LLC, Chicago, IL (US)

(*) Notice: Subject to any disclaimer, the term of this patent is extended or adjusted under 35 U.S.C. 154(b) by 1160 days.

(21) Appl. No.: 16/146,970

(22) Filed: Sep. 28, 2018

(65) Prior Publication Data
US 2019/0294758 A1      Sep. 26, 2019

Related U.S. Application Data

(63) Continuation of application No. 15/936,329, filed on Mar. 26, 2018, now Pat. No. 11,380,422.

(51) Int. Cl.
*G16C 20/30*    (2019.01)
*G06N 3/04*     (2023.01)
(Continued)

(52) U.S. Cl.
CPC ............... *G16C 20/30* (2019.02); *G06N 3/04* (2013.01); *G06N 3/08* (2013.01); *G16C 20/20* (2019.02); *G16C 20/70* (2019.02)

(58) Field of Classification Search
CPC ........ G16C 20/30; G16C 20/20; G16C 20/70; G06N 3/04; G06N 3/08
See application file for complete search history.

(56) References Cited

U.S. PATENT DOCUMENTS

| | | | | |
|---|---|---|---|---|
| 5,218,529 A | * | 6/1993 | Meyer | G06F 15/42 364/413.01 |
| 5,548,217 A | * | 8/1996 | Gibson | G01R 33/20 324/316 |
| 5,761,383 A | * | 6/1998 | Engel | G06F 15/18 395/21 |

(Continued)

OTHER PUBLICATIONS

"Autofit, an automated triples fitting program for broadband rotational spectroscopy," http://faculty.virginia.edu/bpate-lab/autofit/, Copyright 2013, Nathan Seifert.

(Continued)

*Primary Examiner* — Tarun Sinha
*Assistant Examiner* — Lal C Mang
(74) *Attorney, Agent, or Firm* — Marshall, Gerstein & Borun LLP

(57) ABSTRACT

A method of identifying molecular parameters in a complex mixture may include receiving a set of combined transition frequencies and analyzing the set of combined transition frequencies using a first trained artificial neural network to generate a plurality of separated transition frequency sets. Each of the plurality of separated frequency sets may be analyzed using a second trained artificial neural network to generate a respective set of estimated spectral parameters. The method may include identifying a set of molecular parameters corresponding to the set of separated transition frequencies.

20 Claims, 26 Drawing Sheets

(51) Int. Cl.
*G06N 3/08*      (2023.01)
*G16C 20/20*     (2019.01)
*G16C 20/70*     (2019.01)

(56)              References Cited

U.S. PATENT DOCUMENTS 5,991,028 A  *  11/1999  Cabib ..................... G01B 9/02
                                                        356/346
2018/0165412 A1 *  6/2018  Frey ....................... G06F 19/22

OTHER PUBLICATIONS

Identifying Broadband Rotational Spectra With Neural Networks, Zalenski, et al., Chemical Sciences and Engineering Division, Argonne National Laboratory, Argonne, IL USA.
Automated Assignment of Rotational Spectra Using Artificial Neural Networks, Zaleski, et al., The Journal of Chemical Physics 149, 104106 (2018).
Artificial Intelligence Characterizes Rotational Spectroscopy, Mary Alexandra Agner, AIP Scilight 2018, AIP Publishing, Sep. 13, 2018.
Gas Phase Chemical Physics Program, DOE Principal Investigators' Abstracts, Chemical Sciences, Giosciences, and Biosciences Division, Office of Basic Energy Sciences, Office of Science, U.S. Department of Energy, May 2017.
Identifying Broadband Rotational Spectra With Neural Networks, Zaleski, et al., Chemical Sciences and Engineering devision, Argonne National Laboratory, Argonne, IL.
Identifying Broadband Rotational Spectra With Neural Networks, Daniel P. Zaleski, retrieved from: http://hdl.handle.net/2142/97003 retrieved on Oct. 10, 2018.

\* cited by examiner

|  | training (s)[a] | prediction (μs)[b] |
|---|---|---|
| linear | 5 | 47(3) |
| symmetric | 179 | 47(3) |
| linear(I=1) | 180 | 47(3) |
| linear(I=3/2) | 393 | 48(3) |
| symmetric(I=1) | 581 | 49(3) |
| symmetric(I=5/2) | 999 | 54(6) |
| a-type | 1619 | 45(3) |
| c-type | 1659 | 46(3) |
| b-type | 2509 | 46(2) |
| a-type(I=1) | 3630 | 48(2) |

[a] includes generating the training set

[b] based on 100,000 executions

Numbers in parentheses represent 1σ uncertainties.

FIG. 7

Training Example

| In |
|---|
| 4000 |
| 7000 |
| 8000 |
| 12000 |
| 14000 |
| 16000 |
| 20000 |
| 21000 |
| 28000 |
| 35000 |

| Out | |
|---|---|
| 4000 | 7000 |
| 8000 | 14000 |
| 12000 | 21000 |
| 16000 | 28000 |
| 20000 | 35000 |

Separation Example

| In |
|---|
| 9000 |
| 10000 |
| 18000 |
| 20000 |
| 27000 |
| 30000 |
| 36000 |
| 40000 |
| 45000 |
| 50000 |

| Out | |
|---|---|
| 9000 | 10000 |
| 18000 | 20000 |
| 27000 | 30000 |
| 36000 | 40000 |
| 45000 | 50000 |

FIG. 11 C

IDENTIFICATION AND LOCALIZATION OF ROTATIONAL SPECTRA USING RECURRENT NEURAL NETWORKS

CROSS-REFERENCE TO RELATED APPLICATION

The present application is a Continuation-in-Part of U.S. application Ser. No. 15/936,329, filed Mar. 26, 2018.

This invention was made with government support under Contract No. DE-AC02-06CH11357 awarded by the United States Department of Energy. The government has certain rights in the invention.

TECHNICAL FIELD

The present disclosure is generally directed to identification and assignment of rotationally resolved spectra using artificial neural networks, in particular, molecular identification based on analysis of rotational spectra using artificial neural networks.

BACKGROUND

Microwave rotational spectroscopy is a technique in which the energy of rotational transitions for molecules in the gas phase is measured using microwave radiation. The technique has been known for over 50 years. Historically, instrumentation and analysis of data output by rotational spectrometers has been complicated, in part due to the voluminous data created during operation of rotational spectrometers. Recently, advances in instrumentation have allowed broadband rotational spectrometers to become commercially available and to be deployed in multiple industries (e.g., pharmaceutical, energy, military, etc.). However, analysis of data output by rotational spectrometers remains complicated and difficult. Only a few skilled analysts worldwide are able to analyze rotational spectra using manual methods, and existing computerized approaches require end users to input many (e.g., fifty or more) parameters manually, may use brute force and/or trial-and-error algorithms, and consequently may have factorial or exponential computational complexity requiring impractical amounts of computation time (e.g., days or weeks). Other approaches (e.g., genetic algorithms, cross-correlation, double resonance spectroscopy, and/or integrated software) may suffer from similar limitations. Also, visually identifying a pattern when the dynamic range reaches 1000:1 or larger may be very challenging. In various applications, a need exists to analyze rotational spectra to identify and/or assign molecular data in a way that is accurate and computationally efficient (e.g., capable of being performed in real-time).

BRIEF SUMMARY

In one aspect, a computer-implemented method of identifying molecular parameters, may include receiving a set of observed transition frequencies and generating a plurality of transition frequency sets and a plurality of spectral parameter sets, wherein each of the plurality of transition frequency sets corresponds to a respective one of the plurality of spectral parameter sets, each of the respective ones of the spectral parameter sets is generated according to physics-based constraints, and each of the respective ones of the plurality of transition frequency sets is computed by calculating the Hamiltonian of each respective one of the plurality of spectral parameter sets. The method may further include training an artificial neural network by analyzing at least the plurality of transition frequency sets and the plurality of spectral parameter sets and using the trained artificial neural network to analyze the set of observed transition frequencies to predict a set of estimated spectral parameters. The method may include identifying a set of molecular parameters corresponding to the set of observed transition frequencies by analyzing the set of estimated spectral parameters.

In another aspect, a molecular parameter identification system may include one or more processors, a sensor capable of measuring a sample to produce a set of observed transition frequencies, a user interface via which a user may interact with the molecular parameter identification system, and a spectrum analysis application comprising a set of computer-executable instructions stored on one or more memories, wherein the set of computer-executable instructions, when executed by the one or more processors, cause the molecular parameter identification system to retrieve, from the sensor, a set of observed transition frequencies, identify, by a first trained artificial neural network analyzing the set of observed transition frequencies, a Hamiltonian type corresponding to the set of observed transition frequencies, select a second trained artificial neural network based on the identified Hamiltonian type, analyze, using the second trained artificial neural network, the set of observed transition frequencies to predict a set of estimated spectral parameters; and identify, by analyzing the set of estimated spectral parameters, a set of molecular parameters corresponding to the set of observed transition frequencies.

BRIEF DESCRIPTION OF THE FIGURES

The figures described below depict various aspects of the system and methods disclosed therein. It should be understood that each figure depicts one embodiment of a particular aspect of the disclosed system and methods, and that each of the figures is intended to accord with a possible embodiment thereof. Further, wherever possible, the following description refers to the reference numerals included in the following figures, in which features depicted in multiple figures are designated with consistent reference numerals.

FIG. 7 depicts a table in which, respectively, the training and prediction times are provided with respect to each type of artificial neural network trained using the methods and systems described herein;

FIG. 11B depicts an example training input and example training output used to train an artificial neural network to separate combined spectra of a complex mixture;

FIG. 11C depicts an example of measured data corresponding to a combined spectra of a complex mixture and the resulting corresponding separated spectra produced by a trained artificial neural network;

Figure 1:
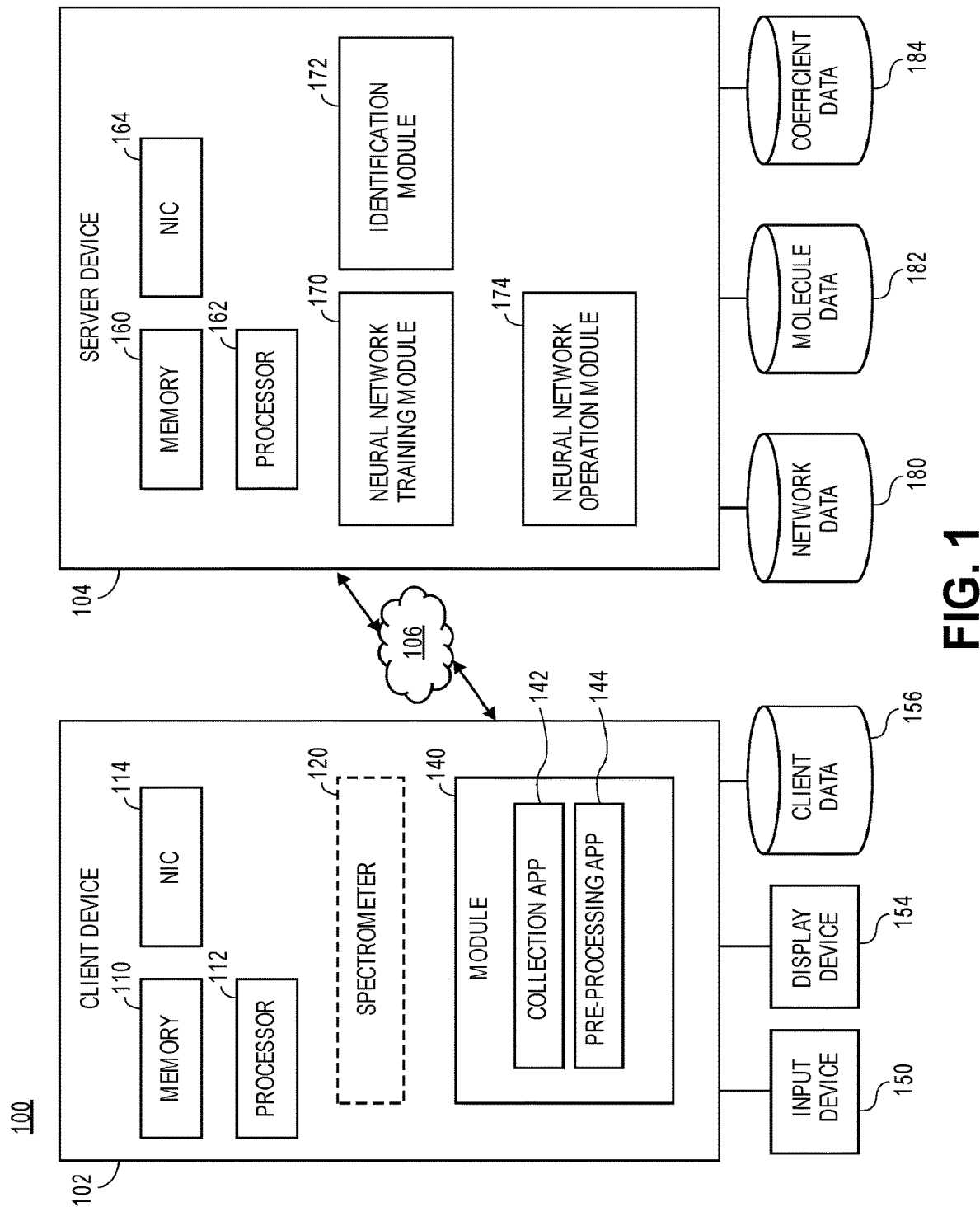
FIG. 1 depicts an exemplary computing environment in which identification and/or assignment of molecular spectra is performed, according to one embodiment.

The figures depict preferred embodiments for purposes of illustration only. One skilled in the art will readily recognize from the following discussion that alternative embodiments of the systems and methods illustrated herein may be employed without departing from the principles of the invention described herein.

DETAILED DESCRIPTION

The embodiments described herein relate to, inter alia, the identification and assignment of rotational spectra. Specifically, machine learning may be used to train a computer to recognize patterns inherent in rotational spectra. Those patterns may be used to assign a spectrum and identify molecular species. A feed forward neural network may be trained to identify different types of rotational spectra and to extract molecular parameters such as rotational constants. Machine learning may also be used to filter and localize the spectra of chemical species included in complex mixtures. In general, the performance of the techniques described herein have far exceeded the inventors' expectations, and commercial interest in the present techniques is strong.

Rotational spectra are understood as rotationally resolved spectra and may include pure rotational spectra and also ro-vibrational (rotational-vibrational) and ro-vibronic (rotational-vibrational-electronic) spectra in which the rotational structure is resolved. The rotational spectrometer is understood as a spectrometer capable of obtaining rotationally resolved spectra, including pure rotational, ro-vibrational and ro-vibronic spectra. The techniques described herein may include training and deployment of artificial neural networks, and may be used in any scenario in which fast and accurate analysis of rotational spectra is desirable. For example, the methods and systems described herein may be used in an analysis pipeline wherein a rotational spectrometer is used to quantify the presence or absence of one or more particular molecules. Herein, a rotational spectrometer may include a rotational spectrometer or another suitable machine. The rotational spectrometer, which may be a microwave rotational spectrometer and/or another type of rotational spectrometer, may include one or more sensors from which data describing the rotational transition spectra of a molecule may be read. Broadband chirped-pulse rotational spectroscopy is a technique that has potential applications in science, engineering, remote sensing, national security, quality control, and other areas. Rotational spectroscopy is preferable to mass spectrometry because rotational spectroscopy is quantitative, conformer- isomer- and, in some cases, enantiomer-specific, and may unambiguously identify chemical substances. Rotational spectroscopy provides quantum state specificity of molecules, which mass spectrometry does not. Further, rotational spectroscopy may completely avoid false positives. Rotational spectroscopy identifies a molecule according to a unique set of rotational transitions, or "fingerprints" of the molecule. Molecules may be specifically identified (e.g., by name and/or chemical formula) and/or may be grouped and/or categorized according to a molecular property and/or attribute (e.g., chiral/non-chiral). An example of an analysis pipelines may include, without limitation, pharmaceutical quality testing, wherein detection of chirality may be highly desirable. Trace detection may be applicable to any domain in which detection of molecules helps to avoid contamination, improve purity, or any other suitable purpose. Another such example may be in the purification and/or analysis of water, wherein one may test for the presence of one or more volatile organic compounds (VOCs). The methods and systems described herein may also be used in the ex post facto analysis of rotational spectra (e.g., data collected from a rotational spectrometer which is stored for later analysis).

Those of skill in the art will appreciate that although the methods and systems described herein are described with respect to certain real-world embodiments, the methods and systems are broadly applicable to any domain in which fact and accurate analysis of rotational spectra is desirable, and that may additional embodiments and applications are envisioned.

Exemplary Computing Environment

FIG. 1 depicts an exemplary computing environment 100 configured to perform identification and/or assignment of molecular spectra. Environment 100 may include a client 102 and a server 104, which may be communicatively coupled by a network 106. Client 102 and/or server 104 may, respectively, be any suitable computing device such as a server device, laptop, smart phone, tablet, wearable device, etc. Network 106 may comprise any suitable network or networks, including a local area network (LAN), wide area network (WAN), Internet, or combination thereof.

Client 102 may include a memory 110 and a processor 112 for storing and executing, respectively, a module 140. Memory 110 may include one or more suitable storage media such as a magnetic storage device, a solid-state drive, random access memory (RAM), etc.; processor 112 may include one or more suitable processors (e.g., central processing units (CPUs) and/or graphics processing units (GPUs)). Client 102 may also include a network interface controller (NIC) 114 and a spectrometer 120. NIC 114 may include any suitable network interface controller(s), and may communicate over network 106 via any suitable wired and/or wireless connection. Spectrometer 120 may be a purpose-built or commercially available spectrometer, and may be integral to client 102 or external to client 102. Spectrometer 120 may be coupled, communicatively and/or physically, to client 102, and may include a chamber for receiving a sample and a facility by which output of analysis performed on the sample may be retrieved (e.g., by processor 112). Module 140, stored in memory 110 as a set of computer-readable instructions, may include a collection app 142 and/or pre-processing app 144 which when executed by processor 112 cause spectrum data and/or metadata to be retrieved or read from spectrometer 120, modified, and/or stored in memory 110. Client 102 may include an input device 150 and a display device 154 by which a user may, respectively, enter input and receive output. In some embodiments, input device 150 and display device 154 may be integrated, such as in a touch screen device. Client 102 may also be communicatively coupled to a client data 156, which may be an electronic database (e.g., structured query language (SQL), key-value, etc.).

Server 104 may include a memory 160 and a processor 162 for storing and executing, respectively, modules. Server 104 may also include a NIC 164, which may include any suitable network interface controller (s), and which may communicate over network 106 via any suitable wired and/or wireless connection. Modules may include an artificial neural network (ANN) training module 170, an identification module 172, and an artificial neural network (ANN) operation module 174. Each of the modules 170-174 may be stored, respectively, in memory 160 as a set of computer-readable instructions. When executed by processor 162, the set of instructions corresponding to ANN training module 170 may generate training data and/or train ANNs. When executed by processor 162, the set of instructions corresponding to identification module 172 may cause molecules to be identified based on coefficient lookup/matching. When executed by processor 162, the set of instructions corresponding to ANN operation module 174 may cause data to be input to a trained ANN, may cause an ANN to be operated, and may cause data to be stored to memory 160 or another location. Server 104 may also include network data 180, molecule data 182, and coefficient data 184.

In operation, ANN training module 170 may train one or more neural networks to receive and process spectrum data, such as data produced by spectrometer 120. First, ANN training module 170 may generate a spectrum training data set with many (e.g., tens of thousands or more) labeled molecules whose structure is chemically plausible but practically imaginary/theoretical. An application and/or program instructions may store the training data set in molecule data 182, and the training data set may represent a universe of molecules that behave according to the known laws/constraints of physics, but which may not exist in reality. It should be appreciated that in some embodiments, the training data set may include molecules that do exist in reality. For example, experimentally measured spectra of real molecules may also be included in the training data set or replace the training data set. Another possibility is that spectra of real molecules are generated using quantum mechanical rules for each type of rotational spectrum, along with an appropriate label (e.g., linear, symmetric, or a-type spectrum). In the latter case, the molecular parameters of those real molecules may either be measured experimentally or predicted from theory, e.g. by solving the Schrödinger equation.

The spectra of real molecules and/or imaginary molecules may be generated using quantum mechanical rules for each type of rotational spectrum, along with an appropriate label (e.g., linear, symmetric, or a-type spectrum).

Each theoretical molecule in molecule data 182 may include a label, which corresponds to a Watson-type Hamiltonian of the molecule and, optionally, includes information regarding perturbation and/or distortion associated with the molecule. A filter that generates (e.g., randomly) scientifically-meaningful/reasonable values within acceptable ranges for parameters may generate the theoretical molecules, and/or may generate transition frequencies based on simulated rotational constants. This generation may include, for each transition, creating matrices that describe the upper and lower states of a system, diagonalizing the matrices, and comparing the upper and lower states to determine a transition frequency. An application may include a list of quantum numbers which describe the energy levels of a set of transitions, wherein the quantum numbers define the structure of the matrices. The generation may further include, for each set of rotational constants, iterating through the list of quantum numbers, calculating the transition frequencies, and adding them to a set of transition frequencies. The end result of this procedure may be a set of sets of transition frequencies, and a set of sets of rotational constants, wherein each one of the set of sets of transition frequencies maps to each respective one of the set of sets of rotational constants. Herein, "Hamiltonian" and "Hamiltonian type" may be used to refer to molecular shape, and may include hyperfine structure, measures of perturbation and distortion, dipole information, spin, rotational selection rules, and any other suitable information for identification and assignment purposes.

ANN training module 170 may create a tiered, and/or hierarchical, ANN wherein the root node of the network comprises a classification ANN (e.g., a multi-layer perceptron feed-forward neural network) trained using the training data set as training input to classify spectrum data according to Hamiltonian type, perturbation, and/or distortion. The ANN may be a network-of-networks. In an embodiment, the ANN, or parts thereof, may be constructed using a compiled programming language for faster execution. The ANN may be trained using supervised learning. Branching from the root node may be regression ANNs that ANN training module 170 may train to predict spectrum parameters based on spectrum inputs. ANN training module 170 may train regression ANNs individually for each distinct Hamiltonian and hyperfine structure using the theoretical molecules described above. Network data 180 may store the trained hierarchical ANN, comprising trained classification ANN and one or more trained regression ANNs.

Once ANN training module 170 fully trains the hierarchical ANN, a user of client 102 may insert a sample into spectrometer 120 and may request an analysis by, for example, interacting with input device 150 and/or display device 154. Spectrometer 120 may perform the requested analysis and either during the analysis, or at the conclusion of the analysis, emit an analysis data set which includes spectrum data. Collection app 142 may receive and/or retrieve the spectrum data and, in some embodiments, pre-processing app 144 may pre-process the spectrum data. Pre-processing may include any suitable operations, such as numerical formatting (e.g., rounding), data validation, alignment, etc. The spectrum data may then be persisted for later analysis by, for example, module 140 writing the data out to memory 110 and/or client data 156. Alternately, or in addition, the spectrum data may be transferred to another computer for further analysis (e.g., by a trained ANN) via network 106. Although the foregoing operation includes a user, in some embodiments, sample analysis may be requested/initiated via automated (e.g., robotic) means.

In some embodiments wherein the spectrum data is transmitted to, and/or retrieved by another computer, the spectrum data may be immediately input into a trained ANN. For example, in an embodiment, ANN operation module 174 may include instructions that, when executed by processor 162, cause a trained ANN to be retrieved from network data 180. The instructions may further include retrieving the spectrum data produced by spectrometer 120, and passing the spectrum data to the trained ANN. The data may be passed all at once or in chunks (e.g., in real-time as the data is produced). The volume of data produced by spectrometers may be large and may require a suitable networking connection (e.g., data may be on the order of terabytes per second or larger). The trained ANN may then analyze the input provided by ANN operation module 174 to produce a set of estimated spectral parameters, which are the molecular coefficients the trained ANN predicts, based on its training on the imaginary data set as previously described.

It should be appreciated that ANN operation module 174 may perform additional functions, such as writing output of the neural network to a database such as coefficient data 184, and creating/storing metadata about the operation of the neural network to a suitable location. For example, in some embodiments, the ANN may keep track of profiling information (e.g., the amount of wall or CPU time that elapses while the ANN is performing certain functions), or other information (memory usage, training weights, predictive confidence, etc.).

Once the trained ANN has classified spectrum data according to its Hamiltonian, and predicted a set of estimated spectral parameters corresponding to the spectrum data, identification module 172 may use the estimated spectral parameters to determine the identity of the molecule corresponding to the spectrum data. Identification module 172 may include computer-readable instructions that, when executed by processor 162, cause coefficient data 184 to be queried, using the estimated spectral parameters as query parameters. Coefficient data 184 may include a table that maps known coefficients to molecules, such that the query issued by identification module 172 selects the name of a molecule based on the set of query parameters (i.e., the estimated spectral parameters). The identity of the molecule corresponding to the classified and regressed spectrum data may be returned by coefficient data 184 to identification module 172, which may include further instructions that when executed by processor 162, cause the molecular identity to be transmitted back to the user, and/or stored in association with the spectrum data produced by spectrometer 120. In some embodiments, classification and/or regression may be performed multiple times, and the results aggregated and/or cross-validated. A web server or other suitable computing software accessible by a mobile computing device may be used to allow a user access to results of the ANN analysis. The mobile computing device may include applications (e.g., iPhone apps, Android APKs, etc.) created for the purpose of training and/or operating trained ANNs, which are made available by the proprietor of the systems and methods described herein for downloaded from an application store, either for a fee or gratis. In some embodiments, the user may be required to login and/or provide authentication information before being able to access ANN training module 170 and/or ANN operation module 174.

Although FIG. 1 depicts a client device and a server device in communication via an electronic computer network, in some embodiments, the client device and the server device may be combined into a single device. Similarly, in some embodiments, ANN operation module 174 may be located in client 102. The client/server architecture, or lack thereof, may depend on the needs of particular applications. For example, in some applications of the technology described herein, network latencies may be unacceptable. For another example, ANN training module 170 may train an ANN in server 104, and serialize and/or store the trained ANN and its parameters in memory 160 and/or network data 180. The trained ANN may then be transmitted by server 104 to client 102, and/or retrieved by client 102. Once retrieved by client 102, an ANN operation module 174 located in client 102 may operate the trained ANN. The structure and functioning of ANNs that may be created by ANN training module 170 and operated by ANN operation module 174 are described further with respect to FIGS. 3, 4, and 5.

Exemplary Data Flow

Figure 2:
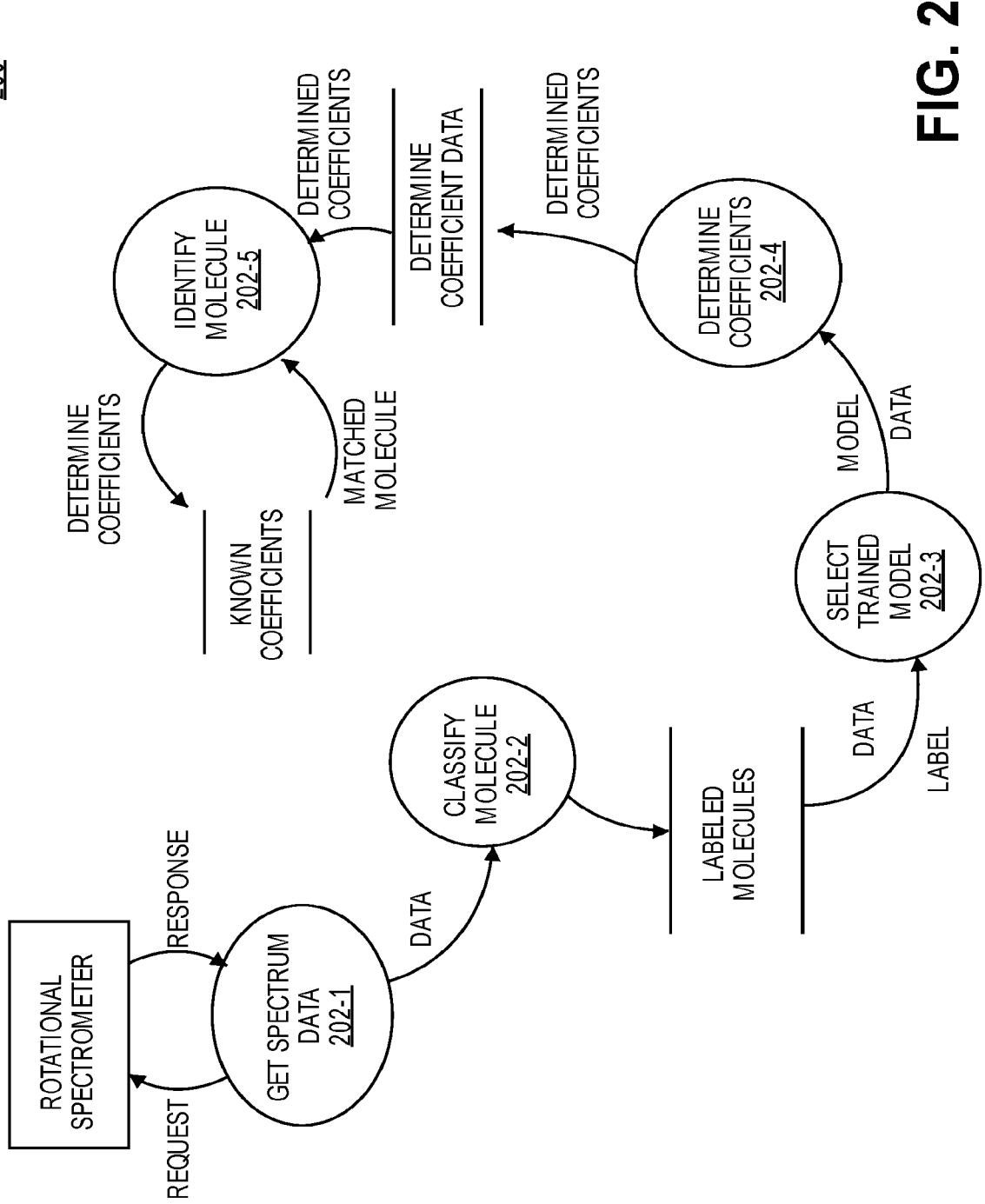
FIG. 2 depicts a flow diagram of an exemplary computer-implemented method by which identification and/or assignment of molecular spectra is performed, according to one embodiment.

FIG. 2 depicts an exemplary data flow diagram 200 of identification and/or assignment of molecular spectra. Data flow diagram 200 may include a set of actions 202-1 through 202-5. In general, actions 202-1 through 202-5 may be performed using ANNs trained by a computing environment such as exemplary computing environment 100. Data flow diagram 200 may include receiving spectrum data action 202-1, wherein requests may be sent to a rotational spectrometer and responses received therefrom. Receiving spectrum data action 202-1 may correspond to module 140, and may emit data which may correspond to the spectrum data described with respect to FIG. 1; specifically, the emitted data may be collected by collection app 142 and pre-processed by pre-processing app 144. Data flow diagram 200 may further include a molecule classification action 202-2 that analyzes the spectrum data and produces a labeled molecule, which includes a label in association with the spectrum data. Data flow diagram 200 may further include a select trained model action 202-3, which is responsible for selecting, from a set of one or more trained models, a trained model corresponding to the labeled molecule. Data flow diagram 200 may further include a determine coefficients action 202-4, which may receive the trained model and the spectrum data, and operate the trained neural network using the spectrum data as input to determine coefficients predicted to correspond to the spectrum data. Data flow diagram 200 may include an identify molecule action 202-5, which may receive determined coefficients and, by querying known coefficients, retrieve a matched molecule.

Exemplary Hierarchical Neural Network

Figure 3:
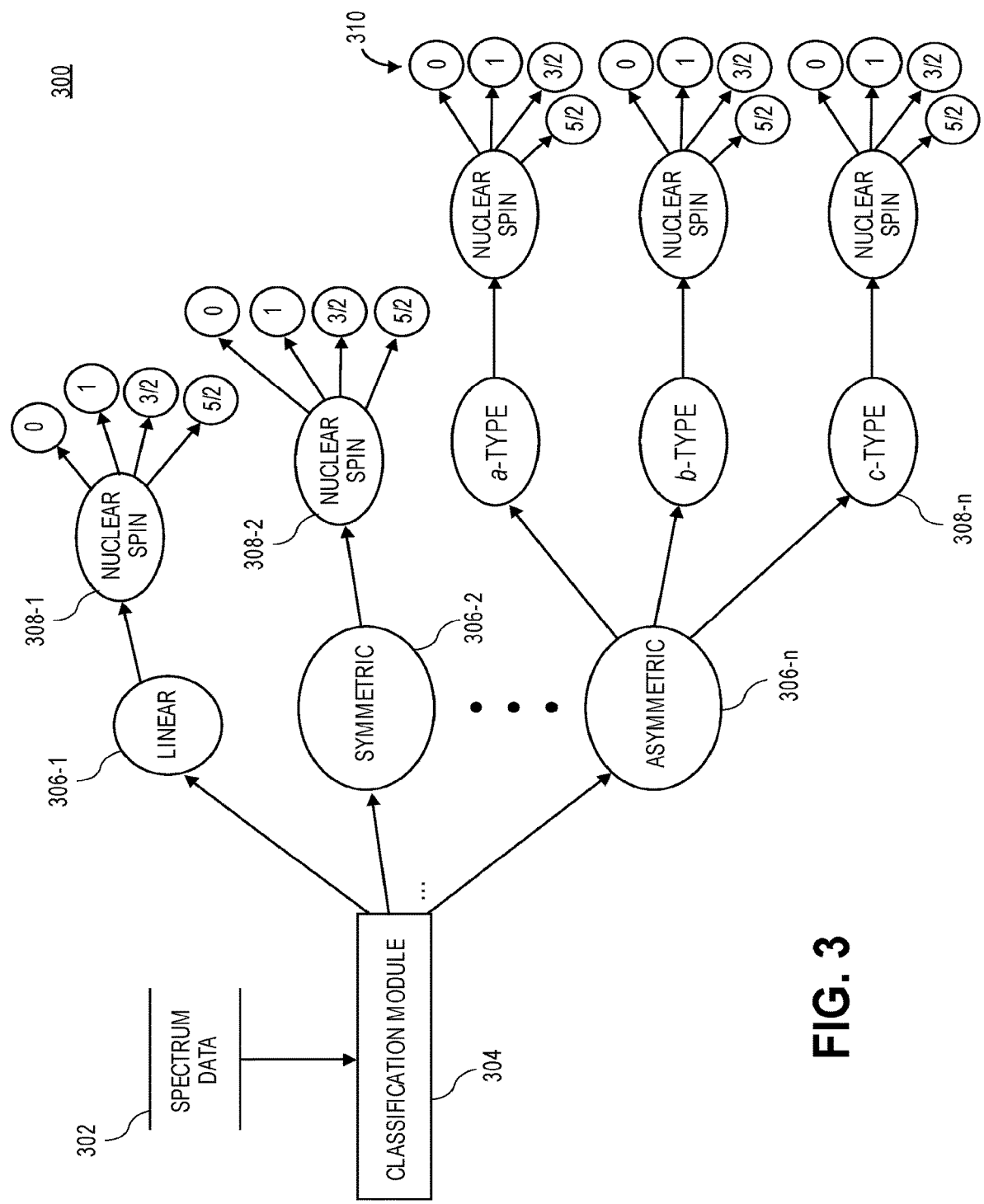
FIG. 3 depicts an exemplary artificial neural network by which molecular spectra are identified and/or assigned, according to one embodiment and scenario.

FIG. 3 depicts an exemplary tiered ANN 300. Tiered ANN 300 may include spectrum data 302, which may correspond to spectrum data produced by spectrometer 120 as described with respect to FIG. 1, and the spectrum data produced by the retrieve spectrum data action 202-1 of FIG. 2. Spectrum data 302 may be stored in a data store such as client data 156, and/or may be streamed via a network such as network 106. Spectrum data may be received by, and/or retrieved by, a classification module 304. Classification module 304 may correspond to a classification ANN trained by ANN training module 170, as described with respect to FIG. 1, and molecule classification action 202-2, as described regarding FIG. 2. Classification module may be the root node of tiered ANN 300, and may be a gate through which all spectrum data 302 must first pass. Classification module 304 may analyze spectrum data 302 to classify spectrum data 302 according to a set of pre-determined labels. The classification may be multi-stage, and a first stage may comprise classifying spectrum data 302 according to one of a plurality of molecular shapes 306-1 through 306-n, wherein n is a positive integer. Each of shapes 306-1 through 306-n may include a respective plurality of additional classification criteria 308-1 through 308-n, including hyperfine structure, nuclear spin, and/or rotational selection rules. For example, node 310 may be an asymmetric molecule of a-TYPE, having a hyperfine structure of I=1, where I is the nuclear spin quantum number. In some cases, hyperfine structure may be included in the composition of the ANN but rotational selection rules may not be, such as in the linear branch of tiered ANN 300. It should be appreciated that additional shapes may be added to shapes 306-1 through 306-n, as needed. Further, it should be appreciated that additional branches may be added to include hybrid spectra (where more than one dipole moment component is non-zero), one-dimensional tunneling, internal rotation, and/or open shell molecules. These separate branches may be added without affecting existing training, and likewise, new ANNs may be trained, and/or retrained, for each respective path through tiered ANN 300, without affecting other branches and/or tiers.

Exemplary Artificial Neural Network

Figure 4:
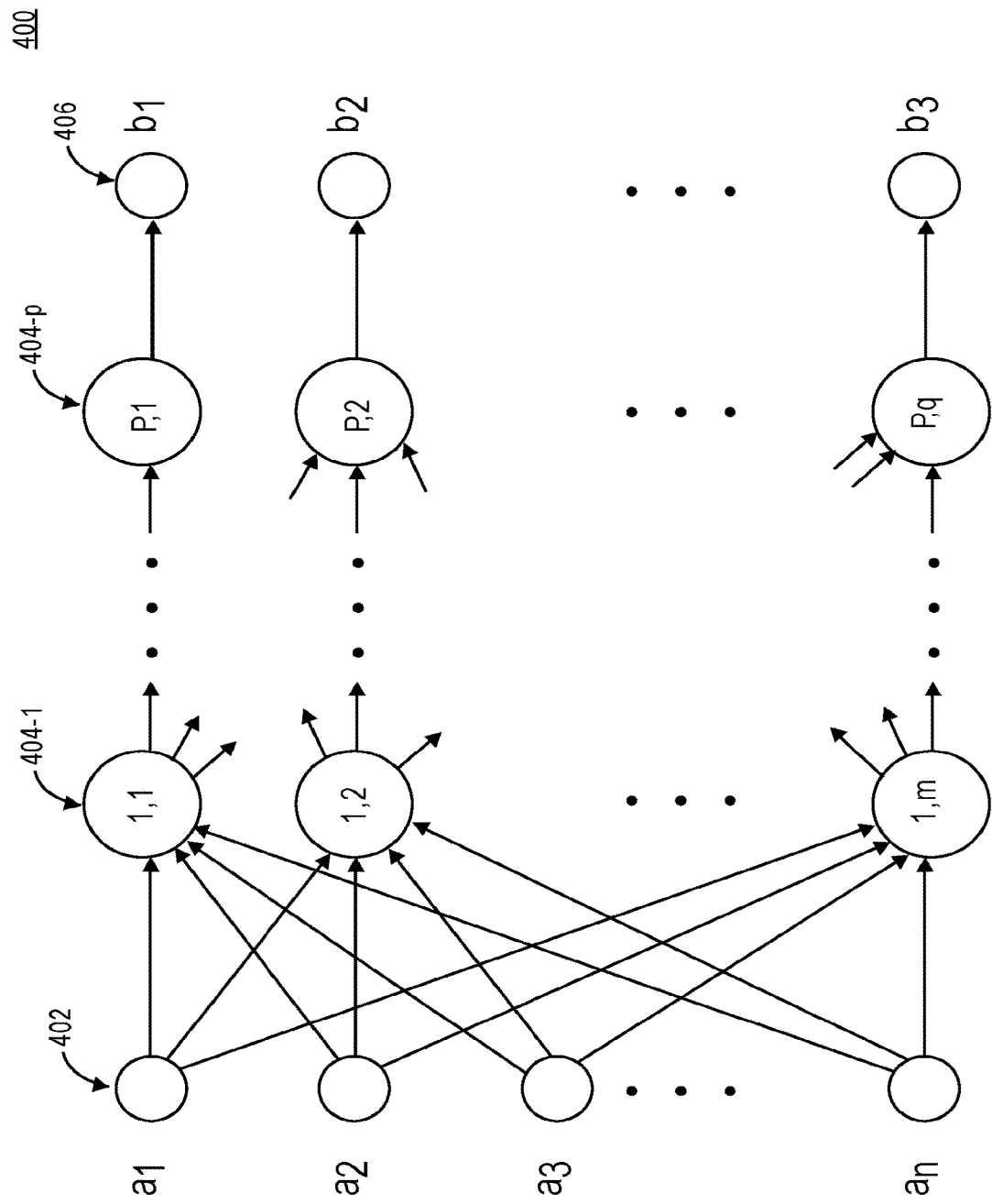
FIG. 4 depicts an exemplary artificial neural network, according to one embodiment.

FIG. 4 depicts an exemplary ANN 400, which ANN training module 170 and ANN operation module 174 of FIG. 1 may, respectively, train and operate. Exemplary ANN 400 may be used to implement molecule classification and/or regression for identification and assignment, according to one embodiment and scenario. ANN 400 may correspond to one or more branches and/or tiers of tiered ANN 300 or, in some embodiments, to tiered ANN 300 in its entirety. Exemplary ANN 400 may include layers of neurons, including input layer 402, one or more hidden layers 404-1 through 404-p, and output layer 406. Input layer 402 may comprise thousands or more inputs. In an embodiment, the number of input parameters may be chosen to be the number of frequencies the network analyzes plus one for a bias, which may correspond to a maximum number of transitions that the network may analyze.

Each layer comprising exemplary ANN 400 may include any number of neurons; i.e., m and q may be any positive integers. The number of parameters used in the hidden layers may be adjusted. In an embodiment, the number of weights created by the ANN as a result of the number of hidden layer parameters may be less than the total number of frequencies being trained on, which may help to avoid overfitting. In an embodiment fewer than four hidden layers may be used. For example, a classification ANN may be trained that consists of an input layer, 2-3 hidden layers, a 10% dropout layer, and an output layer. In that example, a regression ANN may also be trained consisting of an input layer, 2-3 hidden layers, one 10% dropout layer, and an output layer. There, an ANN that fitted two a-type spectra may also be created, as an exception, with five hidden layers. The regression ANN may use "leaky" ReLU activation functions for each layer, and may be compiled using mean squared error (MSE) loss and the Nadam optimizer. Each ANN in the regression ANN may have, for example, a 90:10 validation split, and the input data may be shuffled. Those of skill in the art will appreciate that many different types of learning algorithms, of many different possible structures and configurations, may be used. Those of skill in the art will also appreciate that the depicted exemplary ANN 400 is simplified for expository purposes. Input layer 402 may receive input spectrum data. For example, input 402 may include a first input $a_1$ that corresponds to a Hamiltonian type. Another input $a_2$ may correspond to a set of perturbations associated with a particular molecule. Another plurality of inputs may respectively correspond to spectrum data retrieved from a rotational spectrometer, such as spectrometer 120. In an embodiment, a set of input neurons may be configured to accept intensity information, and another set of input neurons may be configured to accept frequency information. The set of neurons configured to accept intensity information may allow rotational temperature ($T_{rot}$) and/or quantum numbers to be determined with respect to spectrum data inputs. In some embodiments, the number of inputs used by exemplary ANN 400 may change during the training process, and some neurons may be bypassed and/or ignored if, for example, during execution of the ANN, they are determined to be of lesser relevance. It should be appreciated that the methods and systems herein may take advantage of the intensities of transitions in addition to and/or instead of their frequencies, both in training of ANNs and in the analysis of spectra. Learning intensity information, among other things, might allow for inputs of AUTOFIT-type programs to be automatically generated, bypassing the combinatorial search.

In an embodiment, only a single molecule is analyzed. There, a single set of spectral constants may be accepted by input layer 402. In another embodiment, a complex mixture of molecules may be analyzed, in which case a set of sets of spectral constants may be accepted by input layer 402, wherein each neuron in layer 402 may analyze a set within the set of sets of spectral constants. There, pre-processing the spectrum data may include separating the spectrum data into discrete slices or spectral portions before passing the sliced spectrum data into the ANN. In this case, the pre-processing step may include the addition of an ANN. In some embodiments, input neurons may be configured to perform pre-processing, and may correspond to pre-processing app 144. Some additional examples of pre-processing that may be performed include peak picking and/or noise filtering.

Each neuron in hidden layer(s) 404-1 through 404-$p$ may process one or more inputs from input layer 402, and/or one or more outputs from a previous one of the hidden layers to generate a decision or other output. Output layer 406 may include one or more outputs, each indicating a set of coefficients, or estimated spectral parameters, corresponding to data input to input layer 402. In some embodiments, output layer 406 may include a label corresponding to a Hamiltonian of data input to input layer 402. In an embodiment, the number of output nodes may correspond to the number of spectral parameters that are being fit, and the number may vary depending on the Hamiltonian type—a large number of frequencies may be input to the input layer, and a relatively smaller number of spectral parameters may be output by the output layer.

In general, training an ANN may include establishing a network architecture, or topology, adding layers including activation functions for each layer (e.g., a "leaky" rectified linear unit (ReLU), softmax, etc.), loss function, and optimizer. In an embodiment, the ANN may use different activation functions at each layer, or as between hidden layers and the output layer. A suitable optimizer may include Adam and Nadam optimizers. The ANN may be compiled using categorical cross entropy loss. In an embodiment, a different neural network type may be chosen (e.g., a recurrent neural network, deep learning neural network, etc.). Training data may be divided into training, validation, and testing data. For example, 20% of the training data set may be held back for later validation and/or testing. In that example, 80% of the training data set may be used for training. In that example, the training data set data may be shuffled before being so divided. Data input to the artificial neural network may be encoded in an N-dimensional tensor, array, matrix, and/or other suitable data structure. In some embodiments, training may be performed by successive evaluation (e.g., looping) of the network, using training labeled training samples. The process of training the ANN may cause weights, or parameters, of the ANN to be created. The weights may be initialized to random values. The weights may be adjusted as the network is successively trained, by using one of several gradient descent algorithms, to reduce loss and to cause the values output by the network to converge to expected, or "learned", values. In an embodiment, a regression ANN may be used which has no activation function. Therein, input data may be normalized by mean centering, and a mean squared error loss function may be used, in addition to mean absolute error, to determine the appropriate loss as well as to quantify the accuracy of the outputs. Machine learning models may be subject to validation and cross-validation using standard techniques (e.g., by hold-out, K-fold, etc.). The labeled data used to train the ANN may include respective data corresponding to a large group of molecules. In some embodiments, multiple ANNs may be separately trained and/or operated.

The training data itself may consist of thousands (e.g., 40,000 or more) randomly generated stick spectra including frequencies. The size of the training data may be a compromise between performance and training time. Example spectra may be generated in a manner that ensures physicality (e.g. A>B>C, $D_j \geq 0$). For classification ANNs, the examples may be trained alongside a string label (e.g., linear, symmetric, or a-type) which may have been first encoded using a technique called "one hot encoding." For regression ANNs, examples may have been trained alongside the spectral parameters that produced them. Training data sets may be randomly generated for each type of rotational spectrum, along with an appropriate label (e.g., linear, symmetric, and/or a-type spectrum). Additional training sets are also created that exhibit hyperfine structure resulting from one quadrupolar nucleus. After supervised learning, the ANN may be able to distinguish between linear, symmetric, and/or asymmetric tops with 95% certainty or better. With similar performance, the network can also decide whether or not hyperfine structure is present, with I=1, 3/2, or 5/2.

Figure 5:
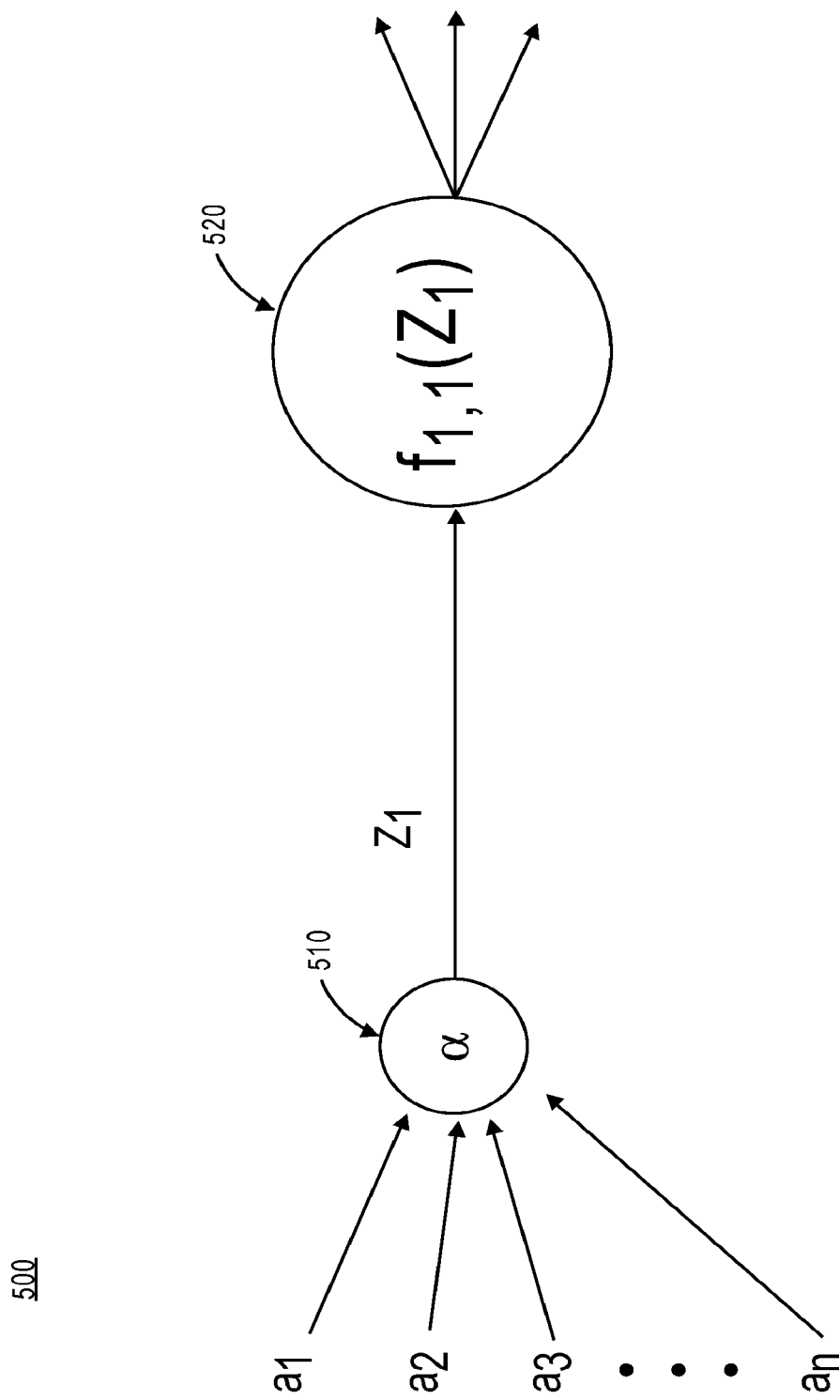
FIG. 5 depicts an exemplary neuron which an artificial neural network, such as the exemplary artificial neural network depicted in FIG. 4, may include.

FIG. 5 depicts an example neuron 500 which may correspond to the neuron labeled "1,1" in hidden layer 404-1 of FIG. 4. Each of the inputs to neuron 500 (e.g., the inputs comprising input layer 402) may be weighted, such that input $a_1$ through $a_n$ corresponds to weights $w_1$ through $w_n$, as determined during the training process of exemplary ANN 400. Weights may be applied to a function 510, $\alpha$, which may be a summation and may produce a value $z_1$, which may be input to a function 520. Function 520 may be any suitable linear or non-linear, or sigmoid, function. In some embodiments, an activation function such as rectified linear unit or softmax may be used. As depicted in FIG. 5, the function 520 may produce multiple outputs, which may be provided as input to neuron(s) of a subsequent layer, or which may represent output of exemplary ANN 400.

In some embodiments, a percentage of the data set used to train exemplary ANN 400 (or other artificial intelligence or machine learning algorithm or model) may be held back as testing data until after the ANN (or other artificial intelligence or machine learning algorithm or model) is trained using the balance of the data set. In embodiments wherein the ANN involves a time series or other temporally-ordered data, all elements composing the testing data set may be posterior of those composing training data set in time.

Exemplary Experimental/Predictive Graphs

Figure 6A:
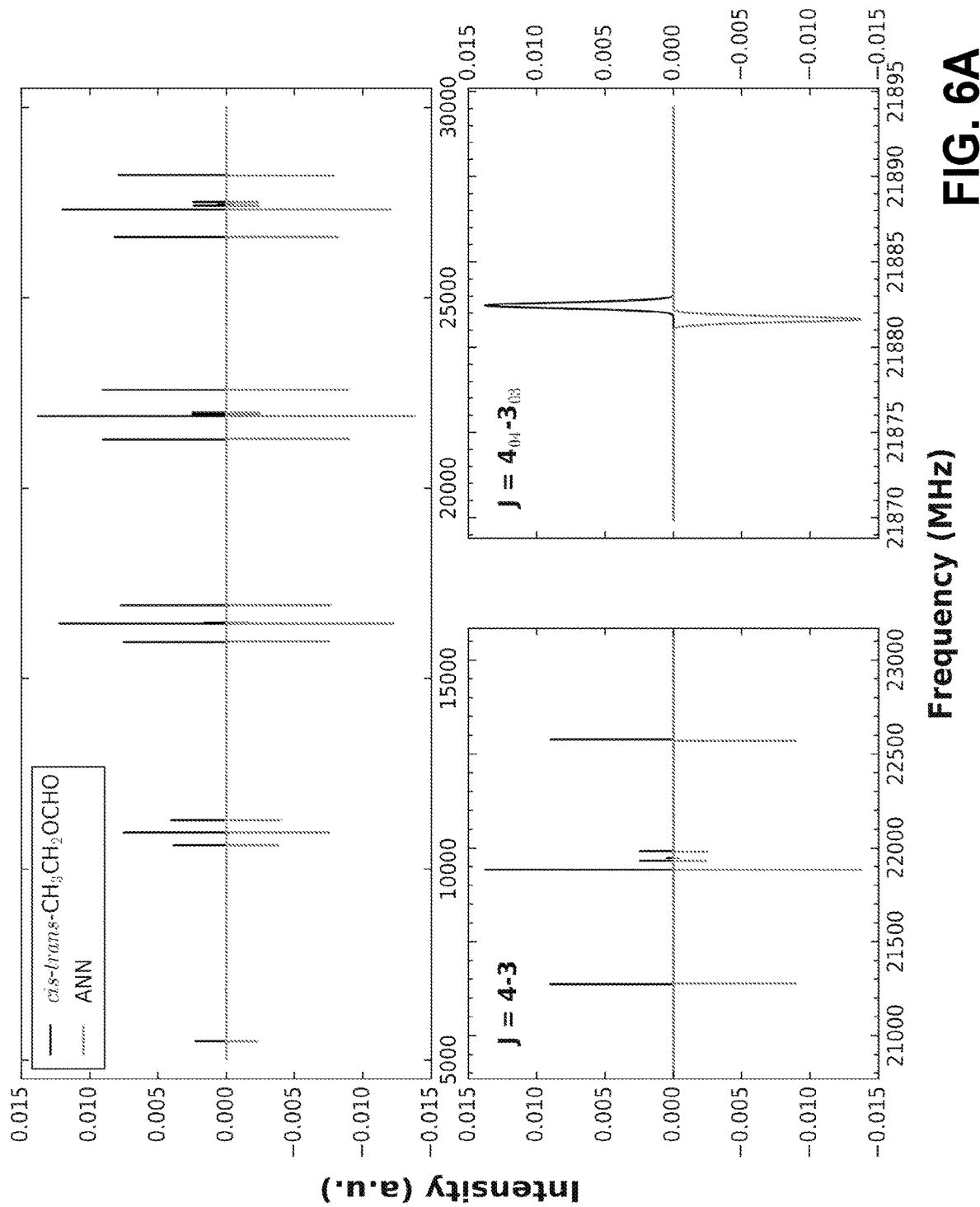
FIG. 6A depicts an exemplary graph in which simulations from known experimental coefficients relating to particular molecules are plotted along the positive Y-axis and simulations from coefficients predicted by the methods and systems described herein are plotted along the negative Y-axis.
Figure 6B:
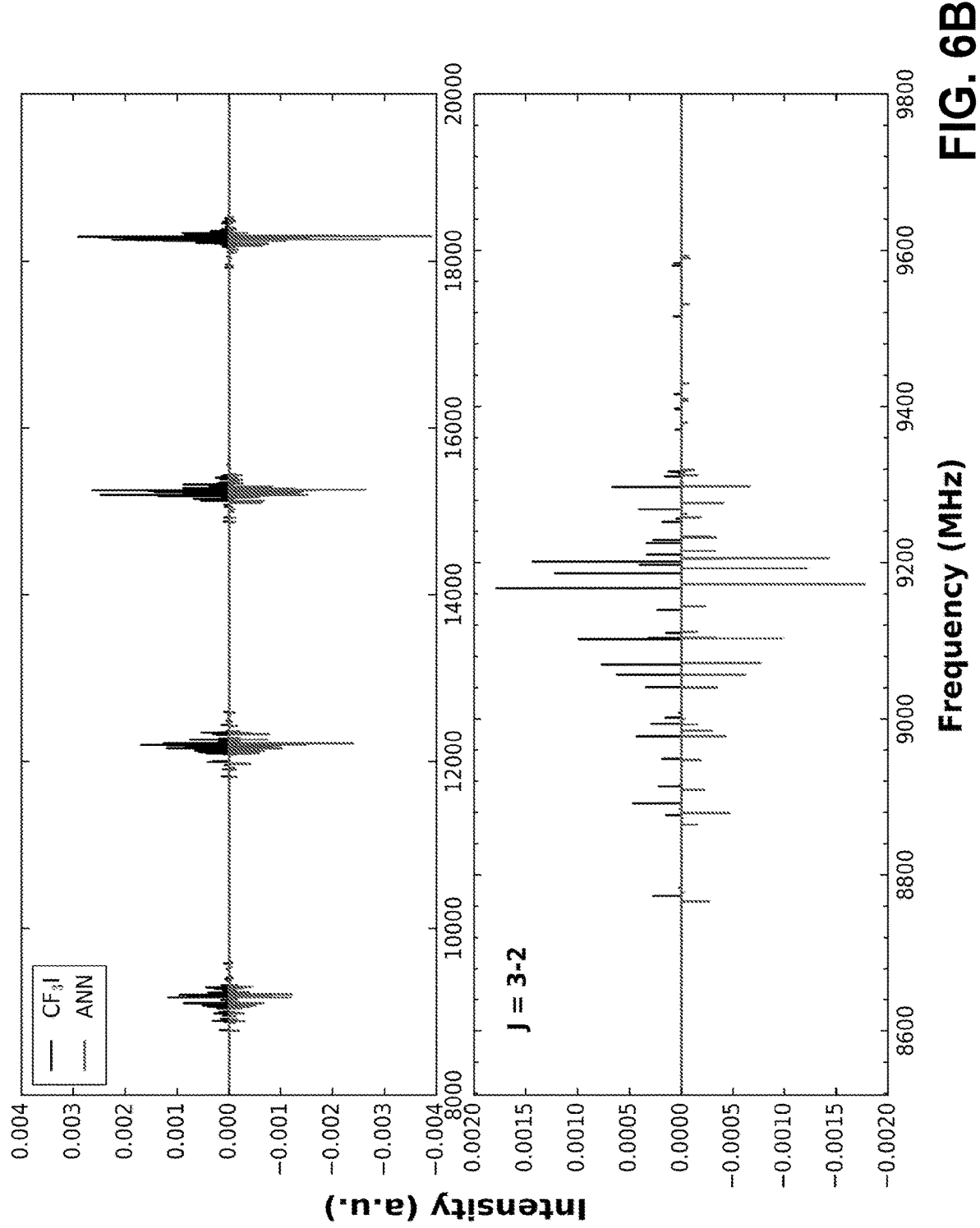
FIG. 6B depicts an exemplary graph in which simulations from known experimental coefficients relating to particular molecules are plotted along the positive Y-axis and simulations from coefficients predicted by the methods and systems described herein are plotted along the negative Y-axis.
Figure 6C:
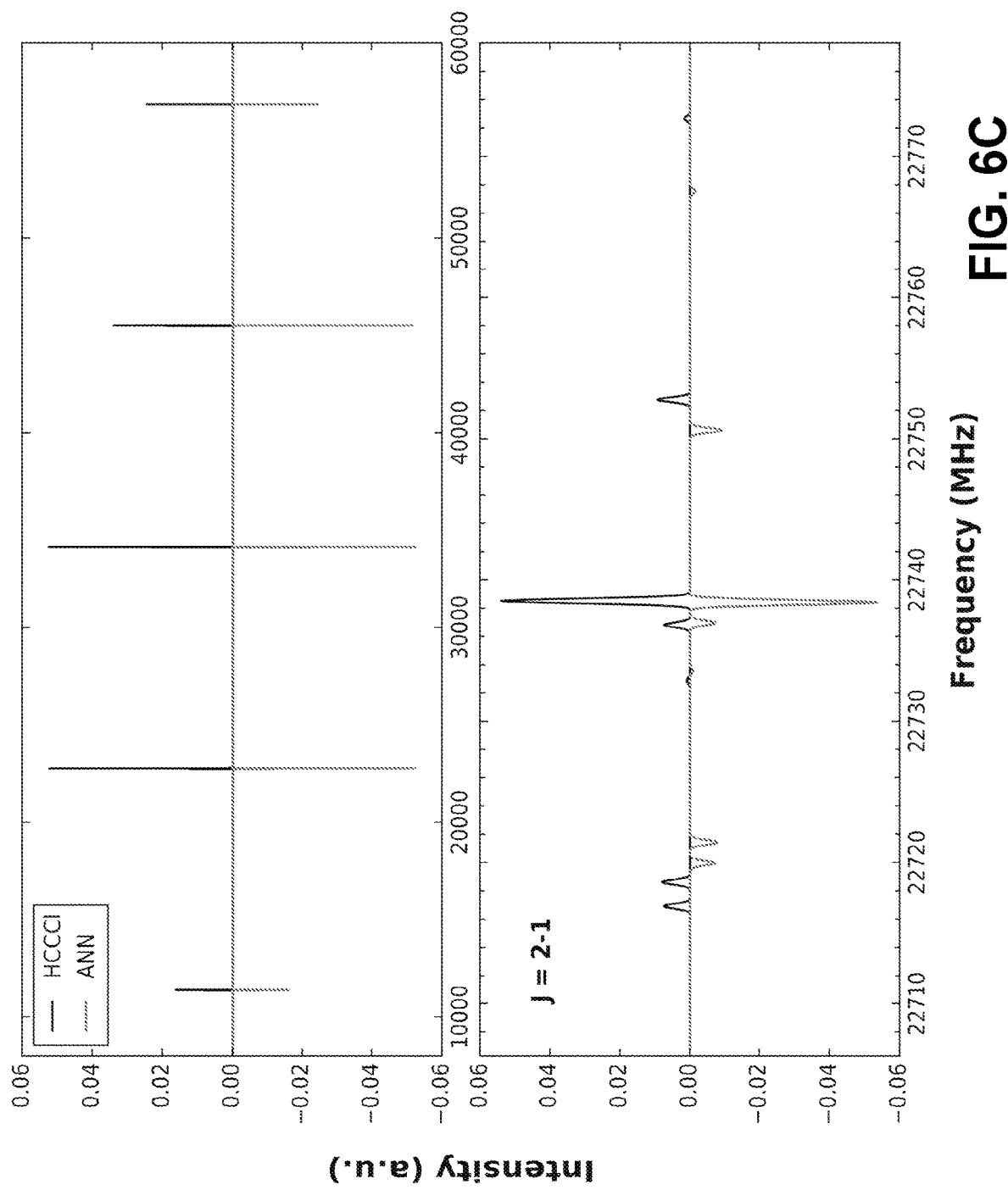
FIG. 6C depicts an exemplary graph in which simulations from known experimental coefficients relating to particular molecules are plotted along the positive Y-axis and simulations from coefficients predicted by the methods and systems described herein are plotted along the negative Y-axis.

FIGS. 6A through 6J depict exemplary graphs in which simulations from known experimental coefficients relating to particular molecules are plotted above the X-axis (i.e., in the positive Y-region of the graph) and simulations from coefficients predicted by the methods and systems described herein are plotted below the X-axis (i.e., in the negative Y-region of the graph). FIG. 6A depicts a simulation based on experimental values of cis-trans-$CH_3CH_2OCHO$ spectrum data against a-TYPE ANN predicted values. The graph includes two sub-graphs for emission lines in the J=4-3 region and J=$4_{04}$-$3_{03}$, both of which show the correlated observed and predicted values at different magnifications. The predicted information may be produced by an ANN corresponding to the a-TYPE ANN depicted as being directly linked to asymmetric shape 306-$n$ in FIG. 3. Turning to FIG. 6B, a graph of a simulation based on experimental values of $CF_3I$ spectrum data against a symmetric ANN predicted spectrum is depicted, according to an embodiment. The graph includes a first sub-graph of frequency spectrum from 8000 to 20000 MHz, and a second sub-graph of frequencies 8600-9800 MHz, wherein emission in the J=3–2 region is depicted. As shown in the graph, the spectral data predicted by the symmetric ANN is strikingly similar to the observed data. FIGS. 6C-6J are similar in that they depict predicted spectra graphed against reproductions of experimental spectra, and that they depict strong correspondence in all cases, both at high and low magnification. Some variance may be observed at high magnification, but the gaps between signals are such that the variances do not interfere with the analyst's ability to quickly confirm results. It should be appreciated that in some embodiments, graphs including some or all of the information of those depicted in FIGS. 6A through 6J may be displayed in a display device of a computing system, such as client 102 of FIG. 1.

Figure 6D:
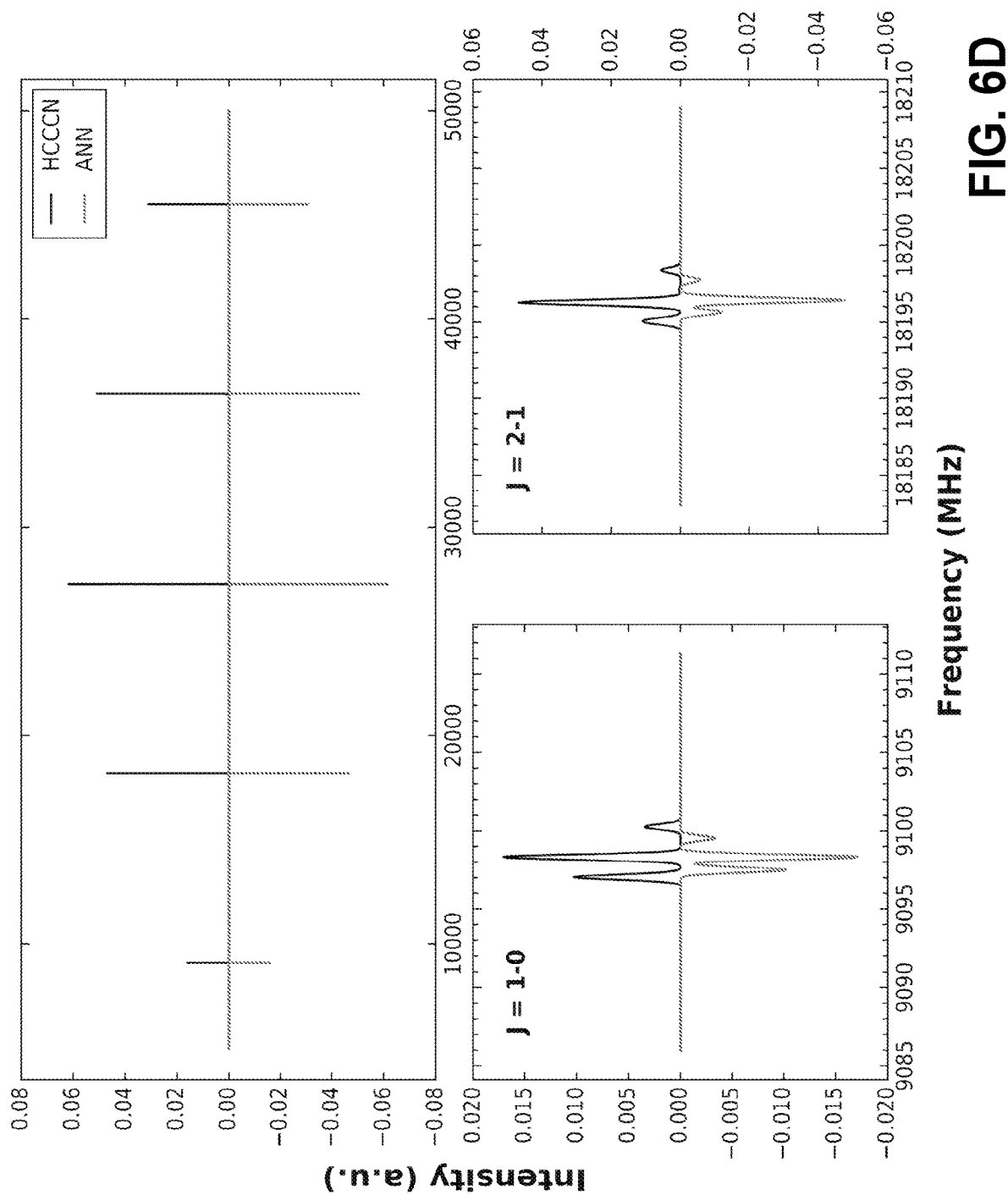
FIG. 6D depicts an exemplary graph in which simulations from known experimental coefficients relating to particular molecules are plotted along the positive Y-axis and simulations from coefficients predicted by the methods and systems described herein are plotted along the negative Y-axis.
Figure 6E:
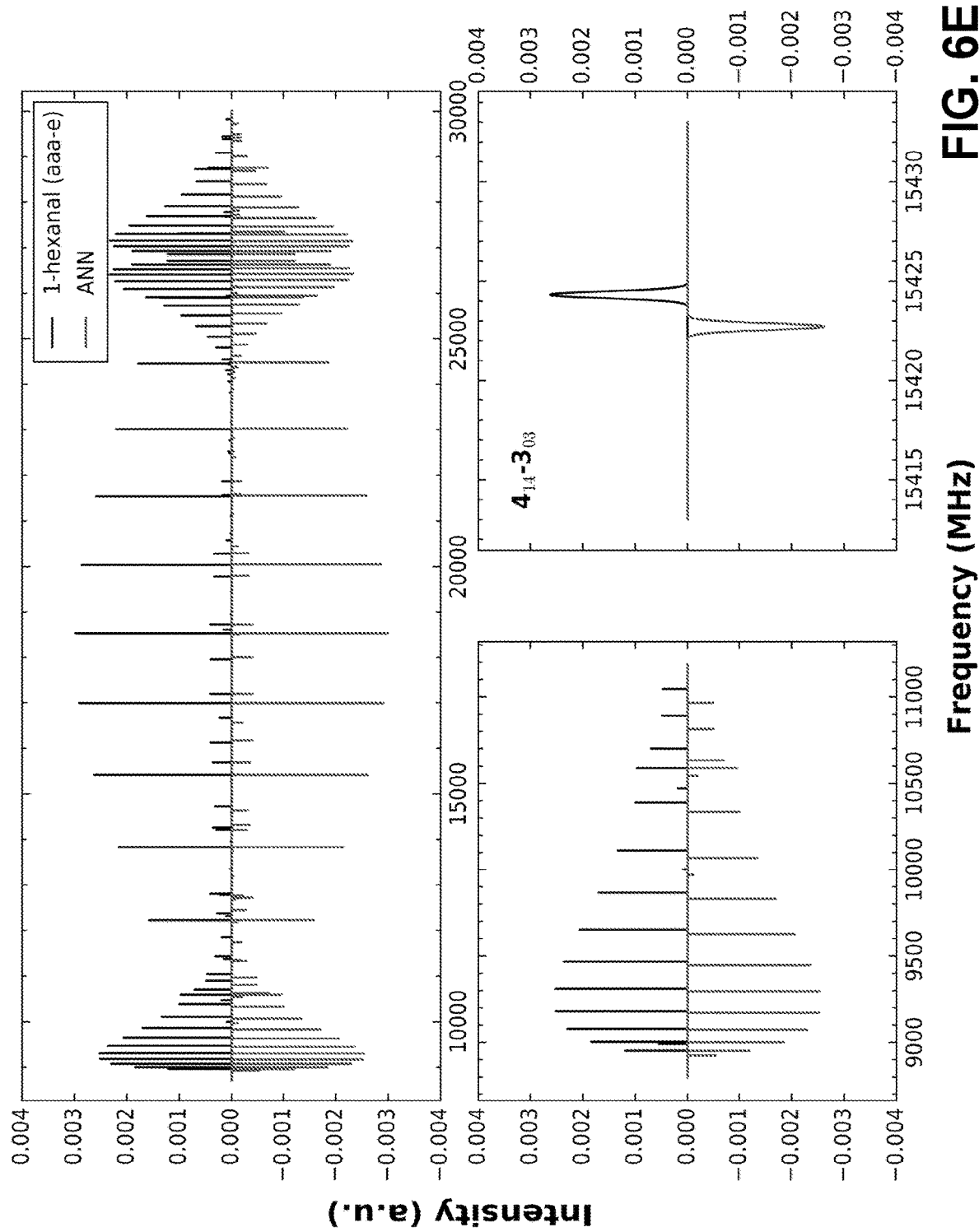
FIG. 6E depicts an exemplary graph in which simulations from known experimental coefficients relating to particular molecules are plotted along the positive Y-axis and simulations from coefficients predicted by the methods and systems described herein are plotted along the negative Y-axis.
Figure 6F:
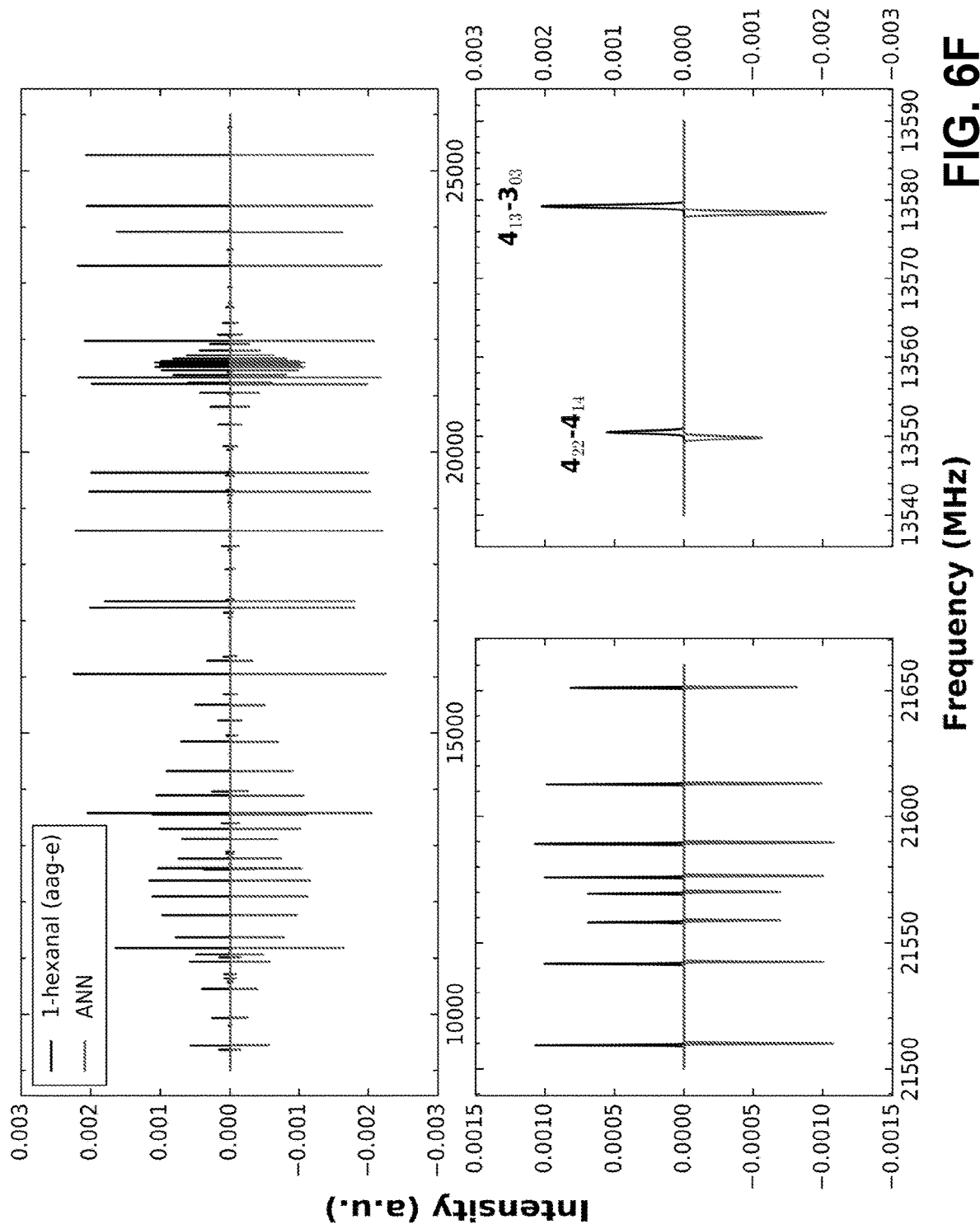
FIG. 6F depicts an exemplary graph in which simulations from known experimental coefficients relating to particular molecules are plotted along the positive Y-axis and simulations from coefficients predicted by the methods and systems described herein are plotted along the negative Y-axis.
Figure 6G:
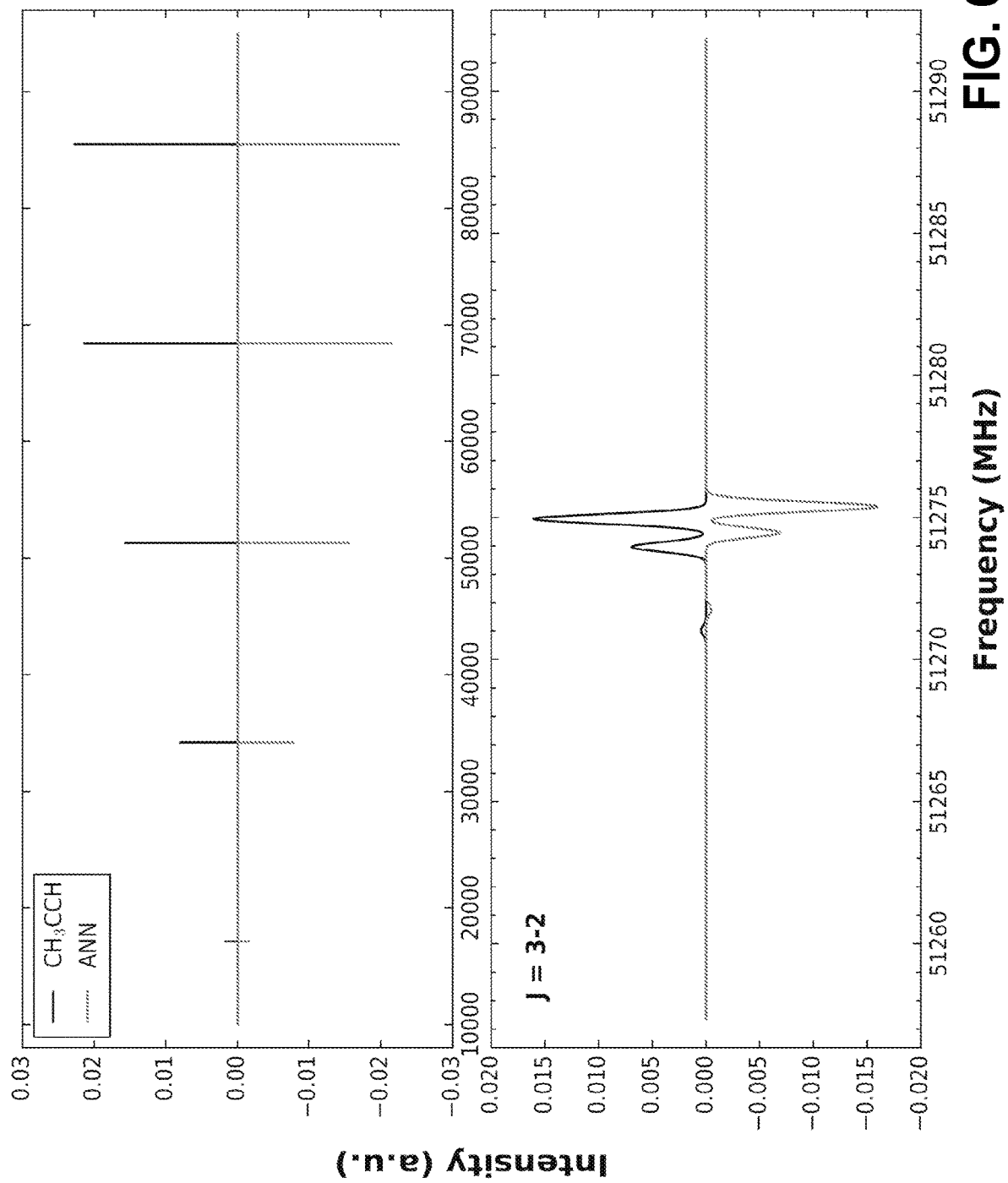
FIG. 6G depicts an exemplary graph in which simulations from known experimental coefficients relating to particular molecules are plotted along the positive Y-axis and simulations from coefficients predicted by the methods and systems described herein are plotted along the negative Y-axis.
Figure 6H:
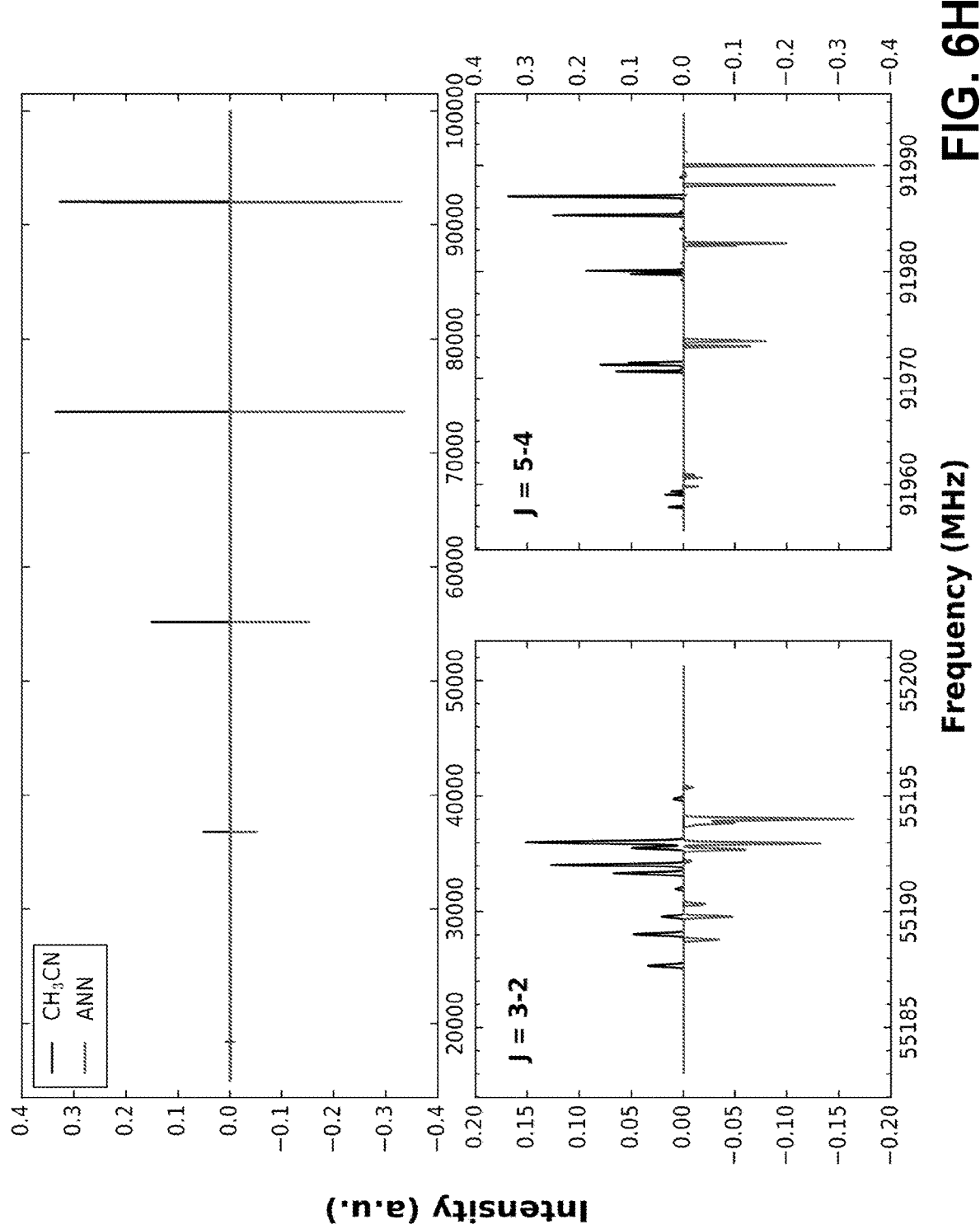
FIG. 6H depicts an exemplary graph in which simulations from known experimental coefficients relating to particular molecules are plotted along the positive Y-axis and simulations from coefficients predicted by the methods and systems described herein are plotted along the negative Y-axis.
Figure 6I:
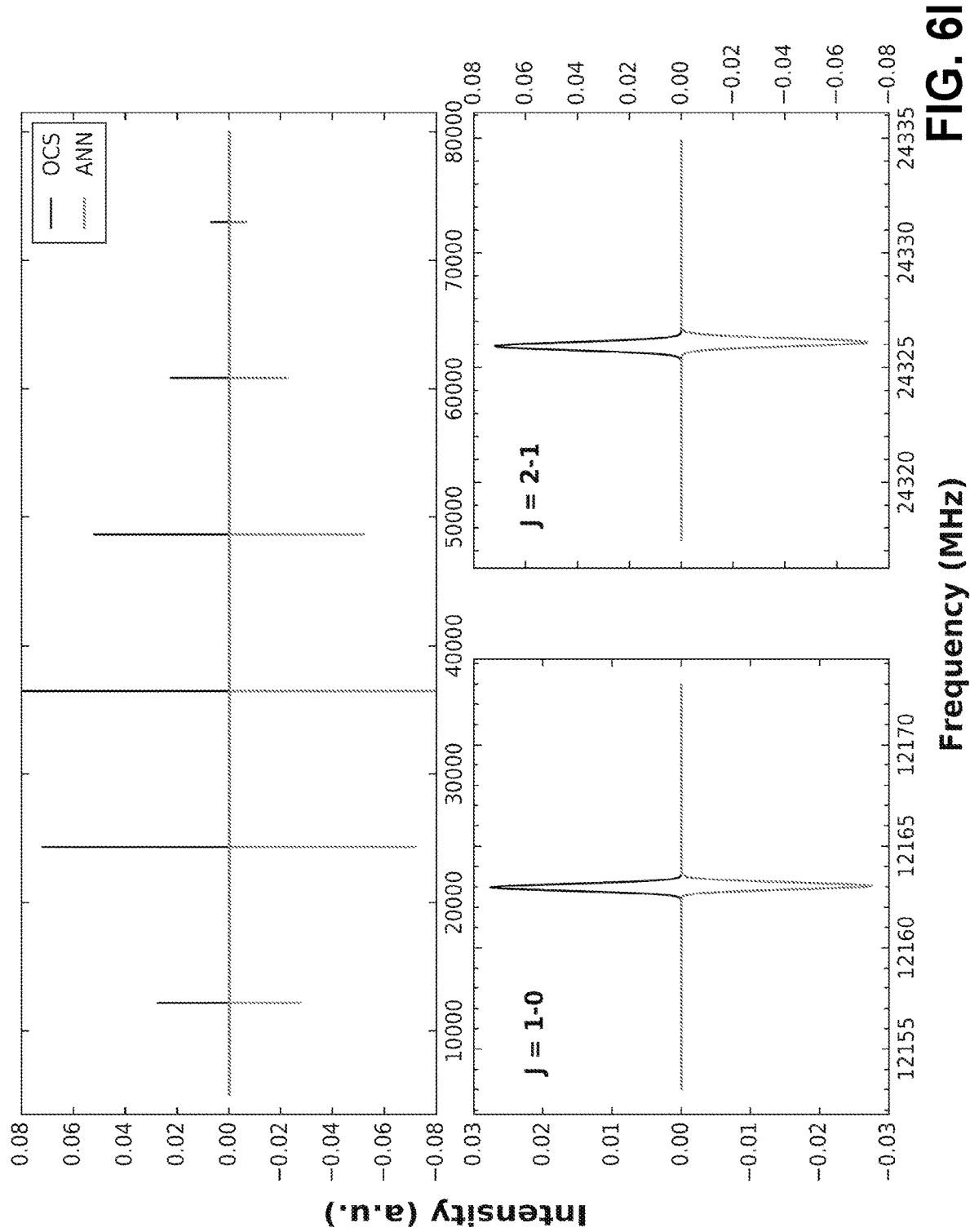
FIG. 6I depicts an exemplary graph in which simulations from known experimental coefficients relating to particular molecules are plotted along the positive Y-axis and simulations from coefficients predicted by the methods and systems described herein are plotted along the negative Y-axis.
Figure 6J:
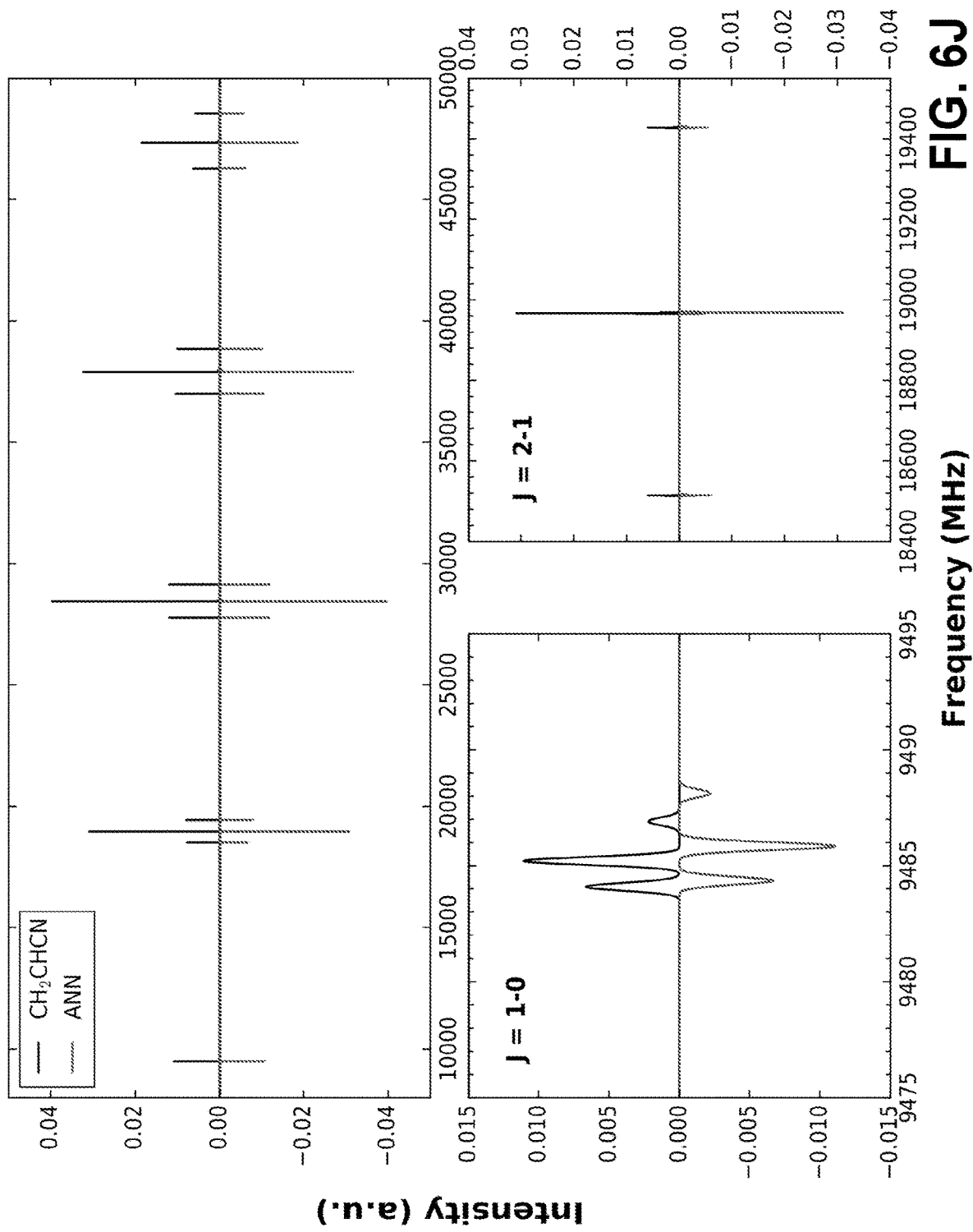
FIG. 6J depicts an exemplary graph in which simulations from known experimental coefficients relating to particular molecules are plotted along the positive Y-axis and simulations from coefficients predicted by the methods and systems described herein are plotted along the negative Y-axis.

In the depicted exemplary graphs, experimentally known constants are plotted against constants fitted by ANNs to give a quick visual reference to a user of whether a match is likely. For example, FIG. 6D depicts a comparison of simulations of HCCCN from experimentally known constants and constants fitted by the ANN. The graph depicts a full-width at half maximum (FWHM) of 400 kHz and $T_{rot}$ of 2K. Table 1 includes a comparison of ANN fit constants and experimental constants for HCCCN.

TABLE 1

| | |
|---|---|
| $B_{ANN}$ (MHz) | 4549.0977 |
| $D_{ANN}$ (kHz) | [0] |
| $eQq_{ANN}$ (MHz) | −2.7248 |
| $B_{exp}$ (MHz) | 4549.058588 |
| $D_{exp}$ (kHz) | 0.5442223 |
| $eQq_{exp}$ (MHz) | −4.3187 |

It should be appreciated that the difference between the fit and experimental constants is negligible, and is measured in kilohertz. HCCCN is a good choice for testing how well the ANN can fit I=1 hyperfine structure, since D<1 kHz. The effects of distortion are quite small, and the agreement is good: $B_{ANN}$=4549.0977 MHz and $B_{exp}$=4549.0586 MHz. The fit of the hyperfine structure is satisfactory: $eQq_{ANN}$=−2.7248 MHz and $eQq_{exp}$=−4.3187 MHz. In all cases, the ANN produces fits that are good enough that the user could tighten them up quickly using standard fitting procedures.

In some embodiments, multiple ANN constants and experimental constants, and/or their differences, may be depicted in tabular and/or graphical format. For example, Table 2 lists a comparison of ANN fit constants and experimental constants for (aag-e) 1-hexanal c-types.

TABLE 2

| | |
|---|---|
| $A_{ANN}$ (MHz) | 5400.7983 |
| $B_{ANN}$ (MHz) | 1143.5070 |
| $C_{ANN}$ (MHz) | 1029.1746 |
| $A_{exp}$ (MHz) | 5399.89397 |
| $B_{exp}$ (MHz) | 1143.248678 |
| $C_{exp}$ (MHz) | 1028.990827 |
| $\Delta_J$(exp) (kHz) | 0.30363 |
| $\Delta_{JK}$(exp) (kHz) | −1.6494 |
| $\Delta_K$(exp) (kHz) | 14.5675 |
| $\delta_J$(exp) (kHz) | 0.064466 |
| $\delta_K$(exp) (kHz) | 1.2275 |

Exemplary Asymptotic Performance

As discussed above, traditional computer-based methods of analyzing rotational spectra may suffer from intractable (e.g., factorial) computational complexity. FIG. 7 depicts exemplary results of ANN training and ANN operation which evince constant-time asymptotic behavior. The first column depicts lists a number of ANN types which are labeled by shape, hyperfine structure, and/or rotational selection rules. The second column lists corresponding training times, in seconds, for each of the respective ANN types in the first column. The third column lists corresponding prediction/operation times, in microseconds, for each of the respective ANN types in the first column. In some embodiments, additional time (e.g., 200 or fewer microseconds) may be used for molecule classification. Unlike traditional methods, the methods and systems described herein are capable of performing identification and/or assignment of rotational spectra very quickly (e.g., in real-time with respect to the operation of a rotational spectrometer). Once trained, the ANNs constructed and operated by the methods and systems described herein analyze identification and assignment tasks much more quickly than a human could, using much more empirical data to provide improved accuracy.

Exemplary Methods

Figure 8:
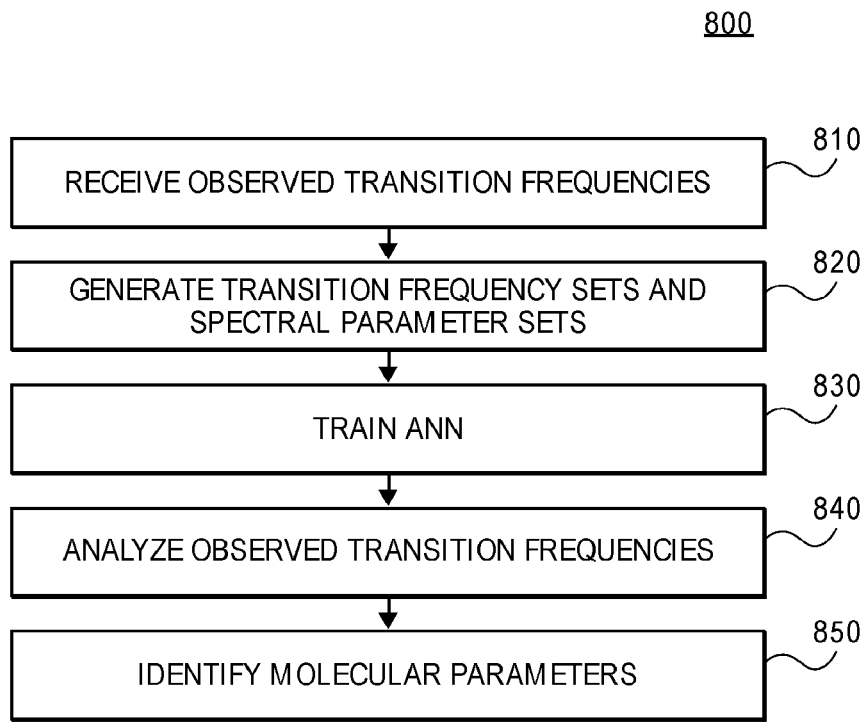
FIG. 8 depicts a method of identifying molecular parameters based on analyzing observed transition frequencies using a trained artificial neural network.

FIG. 8 depicts a flow diagram of a method 800 for identifying molecular parameters based on analyzing observed transition frequencies with a trained neural network. Method 800 may include receiving observed transition frequencies (block 810). The observed transition frequencies may correspond to data produced by rotational spectrometer 120 of FIG. 2 and the rotational spectrometer depicted in conjunction with the retrieve spectrum data action 202-1 of FIG. 2. Method 800 may further include generating transition frequency sets and/or spectral parameter sets (block 820). These sets may be comprised of "imaginary" values that are within a valid range according to the laws and/or theorems of physics and chemistry, but which do not correspond to molecules known via experimentation to exist. Because they include valid physical attributes, they do not describe reality, but are useful in training an ANN to recognize rules that are possible in theory, and thus, to predict one based on the other given new information. Method 800 may include structuring and/or training the ANN, as described above (block 830). Method 800 may further include analyzing the observed transition frequencies using the trained ANN (block 840). The trained ANN may be provided with the observed transition frequencies as input, and may predict a set of estimated spectral parameters based on the prior training with the imaginary values. Method 800 may include identifying one or more molecules based on analyzing the output of the ANN, including the estimated spectral parameters (block 850). Method 800 may include querying a database, flat file, and/or other source of information using the estimated spectral parameters as query parameters, as described with respect to FIG. 2. The result of the query may be a set of one or more molecules having molecular parameters similar to or the same as the estimated spectral parameters. For example, once the type of spectrum is identified, the input data may be fit using a separate ANN for each type of spectrum. The label produced during classification may be used to identify which ANN should be selected. Using that label, the input data may be redirected, and a regression, or fit, performed using the selected ANN. As during classification, the ANNs used for regression may undergo supervised learning. Training sets for regression networks may be generated using similar principles as those used in classification. However, instead of using the Hamiltonian types as labels, the frequencies may instead be trained alongside their spectral parameters. The output of regression networks may then be the fitted spectral parameters. It is easy to envision various network trees that would likely work.

In an embodiment, the output of the ANN may be subject to post-processing (e.g., rounding) during preparation of the query or prior to the query being executed. Insofar as the estimated spectral parameters may be matched and/or correlated to parameters in the source of information, one or more molecules may be positively identified as being present in the sample analyzed by the spectrometer, and the result of the identification may be provided to a user or saved to a database or other information repository. It should be appreciated that in some embodiments, the ANN may produce estimated spectral parameters that are not a precise match for the molecular parameters corresponding to known molecules. In such cases, the estimated spectral parameters may be compared to known molecules to produce a set of candidate matches, wherein a corresponding likelihood of the estimated spectral parameters matching each respective known molecule in the set of candidate matches is generated for each respective known molecule in the set of candidate matches. The methods and systems disclosed herein may allow for identification of a set of molecular parameters corresponding to a set of observed transition frequencies through the analysis of a set of estimated spectral parameters. The analysis may take many forms, including by the relation of deduced approximate molecular parameters to more exact parameters that are known to correspond to certain species. As noted, a typical broadband rotational spectrum may contain several thousand observable transitions, spanning many species. Identifying the individual spectra, particularly when both the dynamic range and the number of resolution elements surpass 10^4, is challenging. By relating the approximate molecular parameters to exact parameters, identification of species may be positively made.

Figure 9:
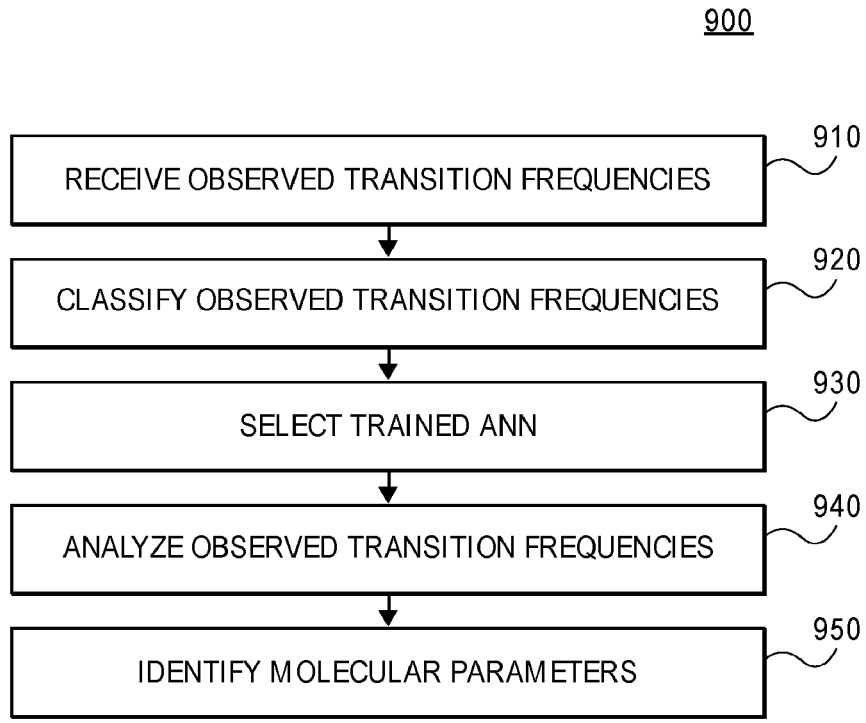
FIG. 9 depicts a method of identifying molecular parameters based on classifying observed transition frequencies using a trained artificial neural network and analyzing observed transition frequencies using a trained neural network.

FIG. 9 depicts a flow diagram of an exemplary method 900 for identifying molecular parameters, according to one embodiment and scenario. Method 900 may include receiving observed transition frequencies (block 910). Method 900 may further include classifying the observed transition frequencies according to shape, hyperfine structure, rotational selection rules, etc., as discussed with respect to classification module 304 of FIG. 3 (block 920). The classification may be performed by a trained ANN, such as the ANN depicted in FIGS. 4 and 5, and may determine a label, such as "SYMMETRIC-HYPERFINE-3/2". In an embodiment, the label may be a set of sub-labels. In method 900, the label may be used to select a trained ANN, wherein the ANN corresponds to the label (block 930). In some embodiments, selection of the trained ANN may comprise navigating to a node in a tree or other hierarchical structure such as tiered ANN 300. Once the trained ANN is selected, the method 900 may include analyzing the observed transition frequencies using the selected trained ANN (block 940). The ANN may have been trained using simulated, or imaginary, spectral data and spectral parameters, as described above. The method 900 may include identifying molecular parameters based on correlating the output of the trained ANN to known molecular parameters (block 950), and as in other embodiments, the result of the identification and/or assignment may be provided to a user, persisted to disk, or used in any other suitable way.

Complex Mixture Analysis

The above discloses, inter alia, methods and systems for the robust identification and localization of a single molecular spectrum. As noted, some embodiments may include analyzing a complex mixture of molecules to disentangle the spectra of specific molecular species. When one or more molecular species are present in the mixed chemical sample, the spectra that belong to different species are often interleaved or mixed. Identifying the rotational transitions with their respective molecular species may be an important prerequisite for further analysis of the mixed chemical sample by means of rotational spectroscopy. For example, some embodiments may include filtering and localizing rotational spectra of chemical species, to enable the conversion of spectroscopic information to chemical species abundances. Filtering out unwanted signals that are inevitable in real-life spectra may dramatically increase the applicability of the present techniques, by allowing the identification of rotational spectra in the field, wherein experimental conditions may be less favorable than in a laboratory setting. As noted, the broadband rotational spectroscopy that underlies such filtering and localizing is rapidly gaining popularity in many areas, including the pharmaceutical, petrochemical, semiconductor, and combustion industries. Specific applications include analyzing oxygenates, ammonia, sour gases, carbon monoxide, oxides of nitrogen, and other polar impurities. Broadband rotational spectroscopy has unique national security applications, and fundamental research/education by government and the academe into broadband rotational spectroscopy is accelerating. There is strong commercial interest in mixture analysis.

Example Complex Mixture Analysis Using Convolutional Neural Network

In an embodiment, the present techniques may include using one or more convolutional neural network (CNN) to localize rotational transitions automatically, thereby separating those transitions from noise, spurious lines, and other unwanted signals. The CNN may be thought of as a front-end to another trained neural network (e.g., an ANN). Another ANN may analyze the localized transitions generated by the one or more CNN to generate spectral assignment and to deduce molecular parameters, as discussed above. For example, the one or more CNN may generate a set of localized transitions, and an ANN trained by training module 170 (e.g., the tiered ANN 300 and/or the ANN 400) may analyze each of the set of localized transitions, to generate a respective spectral assignment and a respective set of molecular parameters corresponding to each of the set of localized transitions. Specifically, the one or more CNN may localize/separate transition frequencies by the application of a number of known techniques, including gradient-weighted class activation mapping (Grad-CAM), convolutional sliding windows, boost cascading, region-based convolutional neural networks (R-CNN), and/or other suitable techniques.

Figure 10:
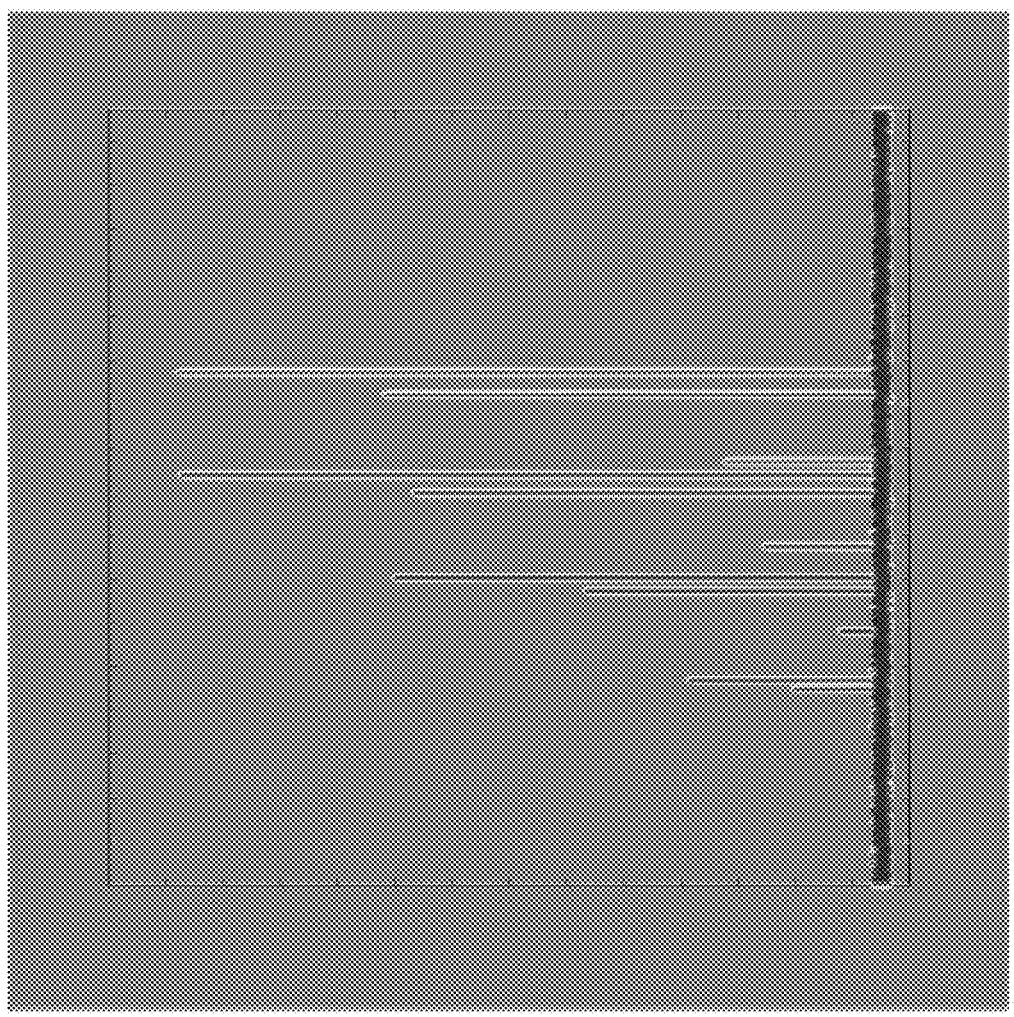
FIG. 10 depicts a heat map of rotational transitions, color-coded according to confidence.

A rotational spectrum may be thought of as an image rather than as an array of transition frequencies. Grad-CAM uses gradients of a rotational spectrum flowing into a network's final convolutional layer to produce a localization map highlighting the important regions of the image. As noted above, training data sets may constructed by randomly generating meaningful rotational constants. Associated spectra may be calculated by adding Gaussian (or other suitable) linewidths, with the distinction that the training spectra are plotted as an N×M pixel image (e.g., 896×896 pixels). FIG. 10 depicts an example of a rotational spectrum of a randomly-generated symmetric top molecule including a random amount of noise. In an embodiment, a CNN highlights the transitions and separates them from the noise and image background. A "heat map" in FIG. 10 reflects confidence of attribution to rotational transitions in the image, with red being most confident and blue being least confident. Although the heat map in FIG. 10 depicts confidence via the use of color, other indications (e.g., textual, numeric, etc.) may be used to depict confidence or other features, in some embodiments.

The CNN is trained by inputting images of spectra resulting from linear molecules, symmetric tops, and/or asymmetric tops, in an embodiment. Other types of molecules may be analyzed, including diatomic molecules, linear molecules, spherical tops, etc. During training, the CNN "sees" images that contain either a spectrum of a linear molecule or a symmetric top molecule. The images may include noise at varying levels of signal-to-noise, thereby facilitating the ability of the CNN to separate transitions (i.e., signal) from noise. In FIG. 10, the CNN identifies rotational transitions in the image of a single spectrum. The heat map indicates the confidence of the CNN that a particular are of the image belongs to a rotational transition of a specific type of molecule. The CNN also outputs a classification label that, in the case of FIG. 10, indicates that the molecule represented in FIG. 10 is a symmetric top molecule. In some embodiments, training the CNN includes training the CNN with images including only noise and no transitions (i.e., absence of any signal). Such images may be referred to as negatives.

The CNN may comprise any suitable structure. For example, layers of the CNN may include 2D zero padding, 2D convolution, 2D zero padding, 2D convolution, and 2D max pooling. There may be, for example, two such blocks. The receptive field size and number of channels may use a deep learning scheme. The final pooling layer may be followed by a block consisting of a flatten layer, three fully connected hidden layers, a 20% dropout layer, and a fully connected output layer. Each layer may use a ReLU activation function, except the output layer, which may employ a softmax activation function. The CNN may be compiled using categorical cross entropy loss and the adam optimizer, may have a 90:10 validation split, and the input data may be \normalized and shuffled. The CNN weights may be used in conjunction with Gradient-weighted Class Activation Mapping, or Grad-CAM, for spectral localization.

The training sets may be created following similar procedures to those outlined above. Once a spectrum is calculated, Gaussian (or other suitable) linewidths may be added. Additional spectra may also be created where a random amount of noise is included. The training set may include spectra of just noise (negatives). Each spectrum may be plotted as an 896×896 pixel image and saved as a Portable Network Graphic (PNG) file. It should be appreciated that any suitably-compressed image file format may be used (e.g., JPEG). The training set may comprise many images (e.g., 1000 or more) of each type. A representative computer used for the training and operation of the artificial neural networks discussed herein may include, for example, an Intel Core i9-7920X CPU; an EVGA NVIDIA GeForce GTX 1080 Ti 11 GB GPU; Crucial DDR4-2666 128 GB (8×16 GB) RAM; a Samsung 960 Pro 2 TB M.2 SSD hard disk; a Gigabyte X299 Designare EX motherboard, and a suitable operating system such as Windows 10 Pro.

The size of images used increases as the resolution of the experimental spectrum increases. The resolution may be computationally expensive. As such, using GPUs may be useful in some embodiments to optimize computation. For example, training on 5000 images may take 550 seconds, with a prediction time of 65 µs, and a mapping time of 230 ms. The memory requirements of the training process may also be computationally expensive. In an embodiment, memory loading can be alleviated by increasing the number of pooling layers (i.e., by downsampling) at the cost of resolution and the benefit of improved generalization. However, when training CNNs to identify rotational transitions, such downsampling may cause line smearing and may thus limit the ability of the CNN to identify interleaved spectra. Notably, CNNs do not require frequency or intensity information on the axes to make an identification. This is because the CNN recognizes the labels as character objects rather than as mathematical quantities. In some embodiments, a post-processing step may include mapping pixels to frequencies.

In summary, CNNs may provide a priori filtering of rotational spectra which may be useful for determining what may or may not be a molecular transition. In contrast to typical object recognition tasks for which CNNs may be used, application of CNNs to rotational spectroscopy is complex due to the common interleaving of the spectra of different molecules. CNNs may be particularly suited for the task of separating rotational transitions that belong to different types of molecules (e.g., linear, symmetric top, etc.) by the distinct patterns corresponding to those types of molecules.

Example Complex Mixture Analysis Using Recurrent Neural Network

Figure 11A:
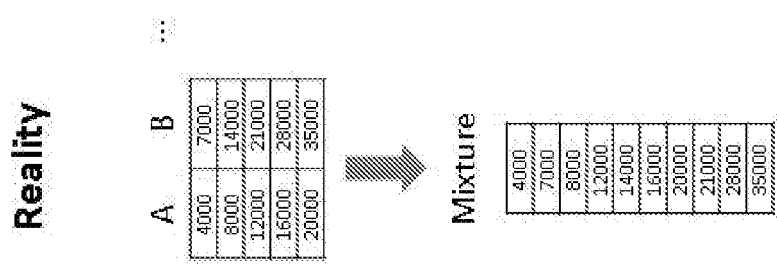
FIG. 11A depicts a hypothetical spectra of two molecules and their respective frequencies combined into a complex mixture.

It has been shown that using CNNs for complex mixture analysis may present some challenges. A recurrent neural network (RNN) may be used instead. In an embodiment, the RNN may include one or more Long Short-Term Memory (LSTM) network layers. FIG. 11A depicts a hypothetical spectra of two molecules A and B. For purposes of illustration, molecule A spectra may include frequencies 4000, 8000, 12000, 16000, and 20000. Molecule B spectra may include frequencies 7000, 14000, 21000, 28000, and 35000. When combined in a complex mixture, molecule A and molecule B combined spectrum may include all of the foregoing frequencies as depicted in the table labeled Mixture in FIG. 11A. An analyst viewing a spectroscopic data of combined molecules A and B would ascertain an undifferentiated frequency spectrum. Adding additional different molecules corresponding to additional frequencies would only complicate the analyst's job. It should be appreciated that while molecules A and B are hypothetical, a complex mixture may include any number of distinct molecules and associated spectra.

FIG. 11B depicts an example of an element that might be included in a training data set for implementing the LSTM layers. For example, a training mixture of a number of molecules may be constructed and used as input. The expected output may be the separated spectra corresponding to the training mixture. Although the input and output in FIG. 11B are depicted as tabular data, the input and output could be represented in any suitable format (e.g., a single vector wherein one spectrum begins after another ends). By analyzing a training data set including many training elements such as the one depicted in FIG. 11B, wherein the training elements each comprise a combined/mixed spectra and the corresponding separated spectra, an LSTM may learn how to separate a mixture into its constituent molecules.

FIG. 11C depicts input of a mixture to the LSTM, which the LSTM has not trained on. The LSTM may recognize that the input comprises subsequences (individual spectra) and attempt to predict which molecules the subsequences correspond to. FIG. 11C depicts the output of the prediction, wherein the subsequences (spectra) are separated. The mechanism of the LSTM is described further below.

Training the LSTM may include selecting a maximum mixture size (Nmax). This may be a number that is larger than the maximum expected number of distinct mixtures likely to be present in any experimental sample (e.g., 100). This number can be increased, and the LSTM retrained. A training data set may be constructed as follows, according to an embodiment. For creating an individual element of the training data set, first pick a random number between 1 and Nmax, wherein the bounds include 1 and Nmax. This random number, N, will correspond to the size of the mixture for the particular element being created. Next, randomly pick a type of molecule (e.g., linear, symmetric, asymmetric, etc.). Then, randomly generate meaningful spectral parameters. The generation of spectral parameters and molecule type may be done according to the principles discussed above, in some embodiments. Next, use the randomly-generated spectral parameters to create a hypothetical spectrum. Repeat the process (starting at randomly picking a type of molecule) N times to create a spectrum having N mixture size for the particular element being created. Each individual calculated combined spectrum may be concatenated and sorted from low to high, in some embodiments. This combined spectrum having N molecules is one element of the training input. The expected training output paired with the training input is the separated spectra corresponding to each of the randomly-generated hypothetical spectral parameters used to create the combined spectrum of N size. As noted, the output may be a tabular format in separate columns, individual spectra lined up one after the other, or in another suitable separated format. If the mixture size that was randomly selected is less than Nmax, then zero padding may be used to fill in "missing" spectra. The maximum length for each individual spectrum may also be controlled, in some embodiments. For example, it may be set to a large number that is unlikely in practice (e.g., 1000). A length for each individual spectrum may be set by random selection, and any elements "missing" (i.e., less than 1000) zero padded. Zero padding according to the foregoing steps maintains the size of the mixture and the length of each individual spectrum. In other words, while the number of trailing zeroes may vary, the overall lengths are the same.

The total size of the training set varies according to the needs of each particular embodiment. However, a training data set of a large size (e.g., 1000-10000) may be sufficient. In summary, each training example may include a random mixture size<=Nmax. Each element of each mixture will be a randomly-selected type of molecule. The spectrum of each randomly-selected molecule will also be of random length. The randomly-generated spectra may be generated according to the principles discussed above. Somewhat counter-intuitively, each mixture may be thought of as a time series. Although the mixture does not correspond to temporal data, by thinking of the mixture as a time series, one can conceptualize that the LSTM makes sequence predictions corresponding to separated spectra across the time series of each mixture.

Figure 12:
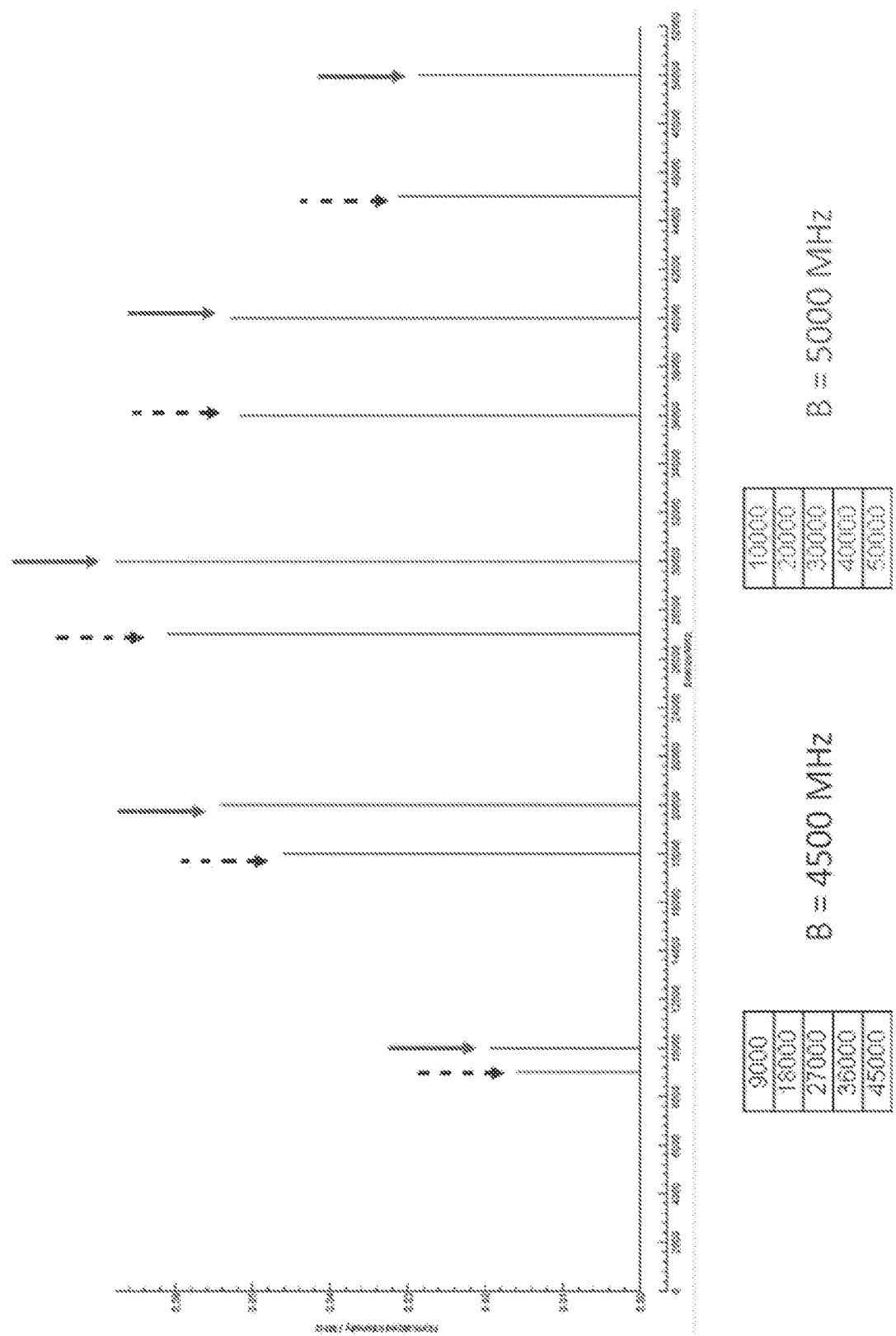
FIG. 12 depicts a graph of two separated spectra wherein dashed and solid arrows denote the respective frequencies included in each of the separate spectra.

FIG. 12 depicts the output of the LSTM described with respect to FIGS. 11A-11C. Specifically, the LSTM outputs a separated list of transition frequencies with respect to each identified molecule included in the complex mixture. FIG. 12 includes two separated spectra corresponding to two hypothetical molecules. The first spectra includes frequencies 9000, 18000, 27000, 36000, and 45000. The second spectra includes frequencies 10000, 20000, 30000, 40000, and 50000. The first and second spectra are plotted using dashed arrows and solid arrows to depict their individual frequencies in FIG. 12. The separated subsequences (i.e., the individual spectra) can be received and/or retrieved by an ANN, such as tiered ANN 300, and analyzed as discussed above with respect to tiered ANN 300, to generate spectral parameters and for identification purposes. The plot of the mixture including highlighted transitions depicted in FIG. 12 could use any other suitable means of denoting the respective spectra, including symbolic and/or structural reference points. Regardless of the particular display mechanism, it should be appreciated that enabling an analyst to see both the spectral parameters and which transitions in the mixture belong to which species is very useful. In some embodiments, the mixture may be plotted after identification has taken place using one or more downstream ANN.

Figure 13:
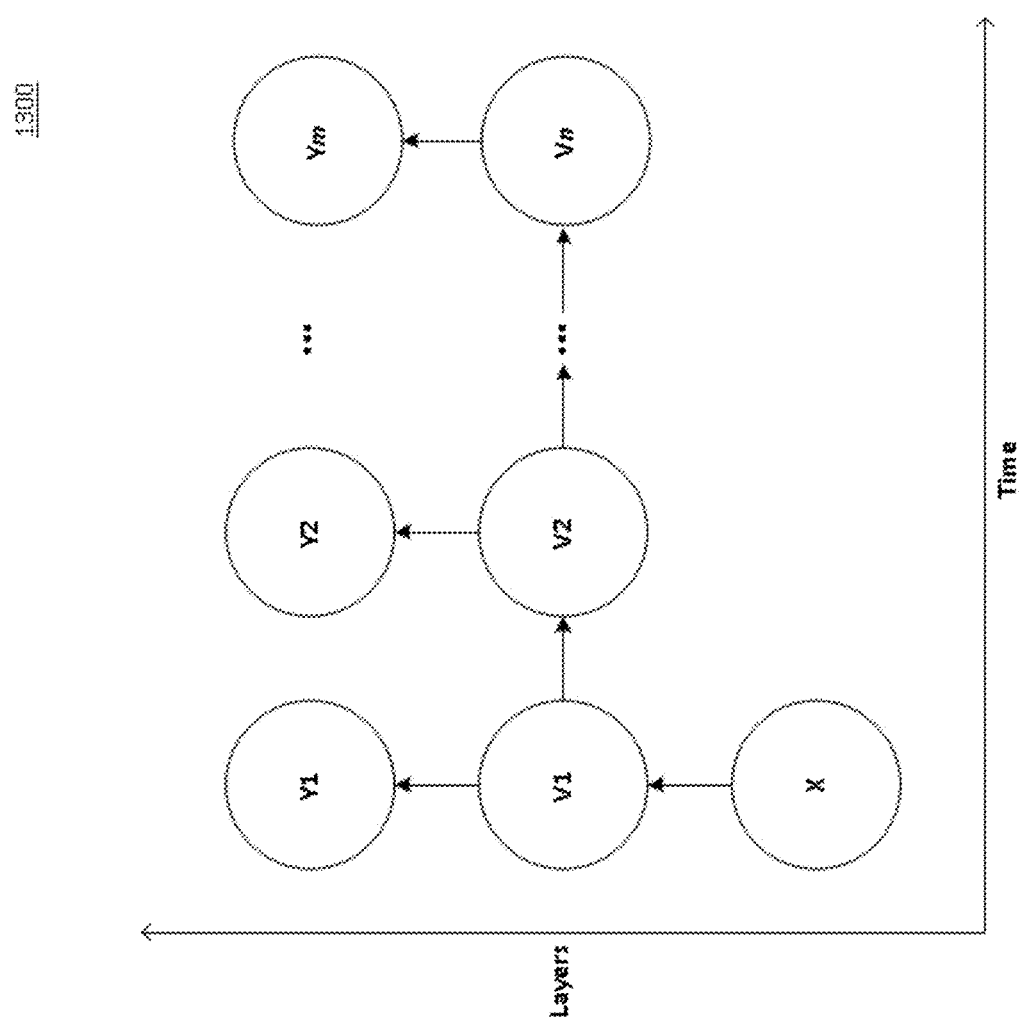
FIG. 13 depicts a one-to-many recurrent neural network wherein a mixture X including a sequence of transition frequencies is mapped to multiple outputs.

FIG. 13 depicts a one-to-many recurrent neural network 1300 wherein a mixture X including a sequence of transition frequencies is mapped to multiple outputs Y1-Ym, wherein each of the multiple outputs corresponds to a distinct spectra found in X. Although a one-to-many RNN is depicted, in some embodiments, RNN 1300 may be a one-to-one RNN or many-to-many RNN. The RNN may include an input neuron X, which receives a list/set of input (e.g., the "In" table of FIG. 11C) corresponding to a set of observed transition frequencies of a complex mixture. For example, the observed transition frequencies may be produced by a rotational spectrometer such as the rotational spectrometer 120 of FIG. 2. In some embodiments, transition frequencies may be taken by multiple machines independently and overlaid to emulate a mixture. In an embodiment, the RNN computes the value of each output Y1-Ym after the value of the respective vector V1-V-n is computed. In another embodiment, the computation of vectors is done first, followed by output computations, such that the RNN computes V1 based on X, V2 based on V1, V2 based on V1, and so on until computing Vn based on Vn−1. The RNN then computes Y1 based on V1, Y2 based on V2, and so on until computing Ym−1 based on Vn−1 and Ym based on Vn. Regardless of the computation plan, the numbers m and n may be any positive integers. Each of the integers 1-n represents a time step, as discussed above. Each output neuron at each time step represents a transition frequency (e.g., 4500 MHz). The numbers n and/or m may correspond to the zero-padded length of the individual spectrum as discussed with respect to FIG. 11, above. As the trained RNN is operated, the first output may be a particular frequency (e.g., 10000). As the RNN continues to execute, the RNN then outputs 20000 at the next time step, based on the learned weights of the RNN and the fact that the previous output was 10000. The RNN is able to separate sequences in this manner by training, and by operation which includes state information from time step to time step. The end result is disentangled spectra, saving analysts countless hours of what would otherwise be error-prone manual methods.

Example of Recognizing Molecular Geometries from Rotational Spectra and/or Molecular Spectra Constants Spectral parameters may include rotational constants, corresponding to the inverse of moments of inertia, and a number of additional parameters such as distortion constants, hyperfine constants, etc. Once the spectral parameters are determined by an ANN through analysis of the rotational transitions, the task is to relate the spectral parameters to molecular geometries and to identify the chemical species that give rise to those rotational transitions. For example, as described with respect to FIG. 8, a method may include providing a trained ANN with observed transition frequencies as input, wherein the ANN may then predict a set of estimated spectral parameters based on the prior training of the ANN using simulated values. The method may include identifying one or more molecules based on analyzing the output of the ANN, including the estimated spectral parameters.

However, relating the spectral parameters to molecular geometries may not result in a single-valued mapping because a single set of spectral constants may correspond to a plurality of molecular geometries or structures (i.e., a set of atoms, bond lengths, and/or angles). A correct correspondence may be discovered. For example, approximate geometries may be determined by reference to constraints on such parameters as atomic mass, bond lengths and angles, valence, molecular orbitals structure, topology of atoms and bonds, location of functional groups. These parameters may be used to train the neural network. A set of hypothetical molecular structures including spectral constants or spectra (i.e., a single-valued function from geometry to moment of inertia/spectral constants or directly to spectra) can be obtained either from a database of molecular species or by imposing physical and chemical constraints on the bond lengths, atomic composition, bond angles, and the topology of atoms and chemical bonds on otherwise randomly generated molecular structures. An artificial neural network can be trained to relate rotational spectra and/or rotational constants to approximate but chemically feasible or exact molecular geometries. For example, generative adversarial networks (GANs) may be used for this purpose. In particular, a GAN may be trained to generate molecular geometries from a large set of feasible and infeasible geometries training data. Next, the trained GANs will be conditioned to produce feasible molecular geometries for given rotational spectra or constants. Such a GAN may be trained using pairs of approximate or exact molecular geometries and rotational spectra. Physical and chemical constraints may be placed on the molecular geometries in the training set or within the GAN. Such constrains may include choosing the feasible atomic masses, bond lengths and/or angles, topology of atoms bonds, and/or functional groups.

Figure 14:
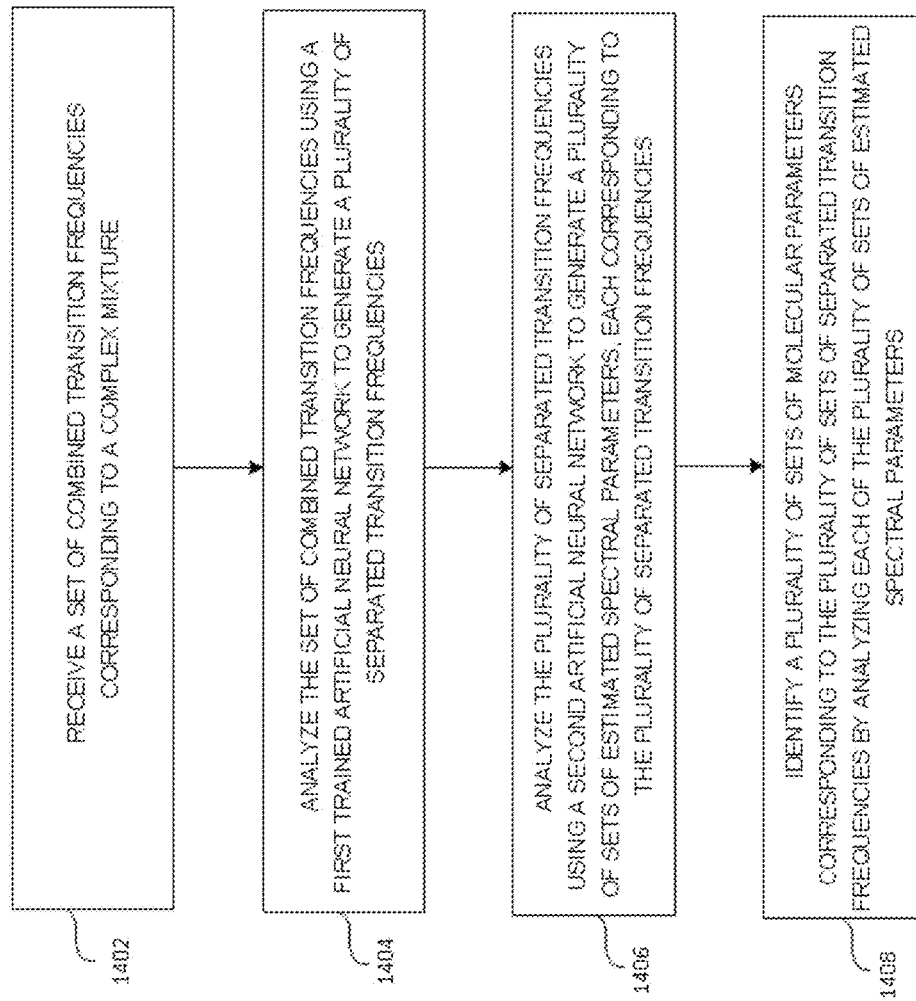
FIG. 14 depicts an exemplary method for identifying molecular parameters corresponding respectively to multiple molecules in a complex mixture.

FIG. 14 depicts a method 1400 of identifying molecular parameters with respect to multiple molecules in a complex mixture. A complex mixture is a mixture of chemical compounds/constituents that may include one or more molecules. For example, a complex mixture may include the elements A and B as depicted in FIG. 11A. In other examples, a large number (e.g., 1000 or more) different molecules may compose the complex mixture. The method 1400 may include receiving/retrieving a set of combined transition frequencies corresponding to a complex mixture (block 1402). For example, one or more microwave spectrometer (e.g., spectrometer 120) may be used to generate a set of transition frequencies corresponding to the molecules comprising the complex mixture. The set of transition frequencies may be received/retrieved via a NIC such as NIC 114. The set of combined transition frequencies may be analyzed using a first trained ANN to generate a plurality of separated transition frequencies (block 1404). The first ANN, which may be an ANN, a CNN, and/or an RNN, may be trained by a training module (e.g., training module 170). The separated frequencies may include sets of frequencies corresponding to a particular molecule as shown in FIG. 11C. The separated frequencies may be plotted as depicted in FIG. 12, saved, and/or analyzed further. For example, the method 1400 may include analyzing the plurality of separated transition frequencies using a second trained ANN to generate a plurality of sets of estimated spectral parameters, each corresponding to the plurality of separated transition frequencies (block 1406). For example, one of the plurality of separated transition frequencies may include {9000, 18000, 27000, 36000, 45000}. This set, and each of the other of the plurality of separate transition frequencies, may be analyzed by the second ANN to produce a set of estimated spectral parameters. The method 1400 may further include identifying a plurality of sets of molecular parameters, each corresponding to one of the plurality of sets of separated transition frequencies by analyzing each of the plurality of sets of estimated spectral parameters. For example, the identification may performed by the identification module 172.

Figure 15:
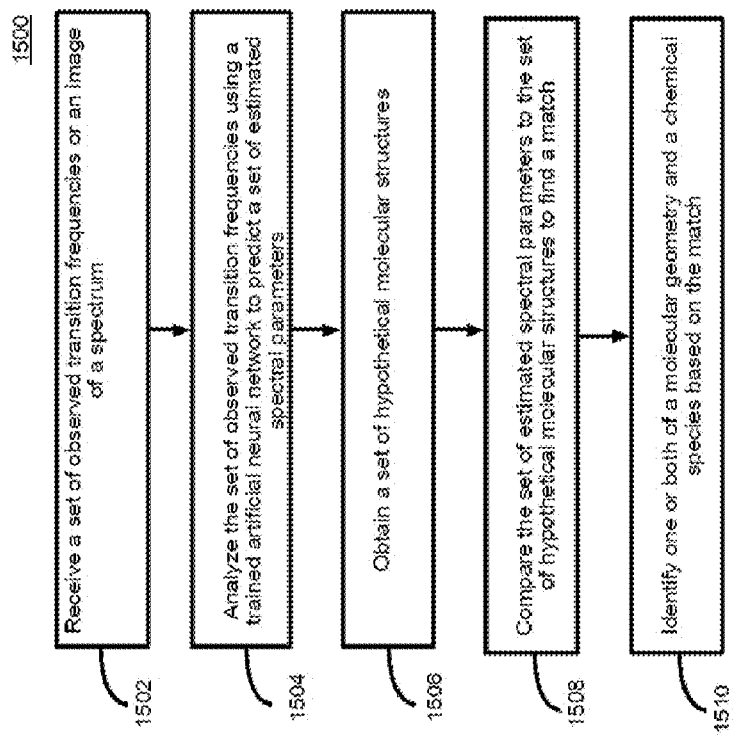
FIG. 15 depicts an exemplary method of identifying molecular geometry and/or a chemical species based on matching a set of estimated spectral parameters to a set of hypothetical molecular structures.

FIG. 15 depicts a method 1500 of identifying molecular geometry and/or a chemical species based on matching a set of estimated spectral parameters to a set of hypothetical molecular structures. The method 1500 may include receiving a set of observed transition frequencies or an image of a spectrum (block 1502). The method 1500 may further include analyzing, using a trained artificial neural network, the set of observed transition frequencies or the image to predict a set of estimated spectral parameters (block 1504). The method 1500 may further include obtaining a set of hypothetical molecular structures (block 1506). The method 1500 may include comparing the set of estimated spectral parameters to the set of hypothetical molecular structures to find a match (block 1508). The method 1500 may include identifying, based on the match, one or both of a molecular geometry corresponding to the estimated spectral parameters, and a chemical species corresponding to the estimated spectral parameters.

Figure 16:
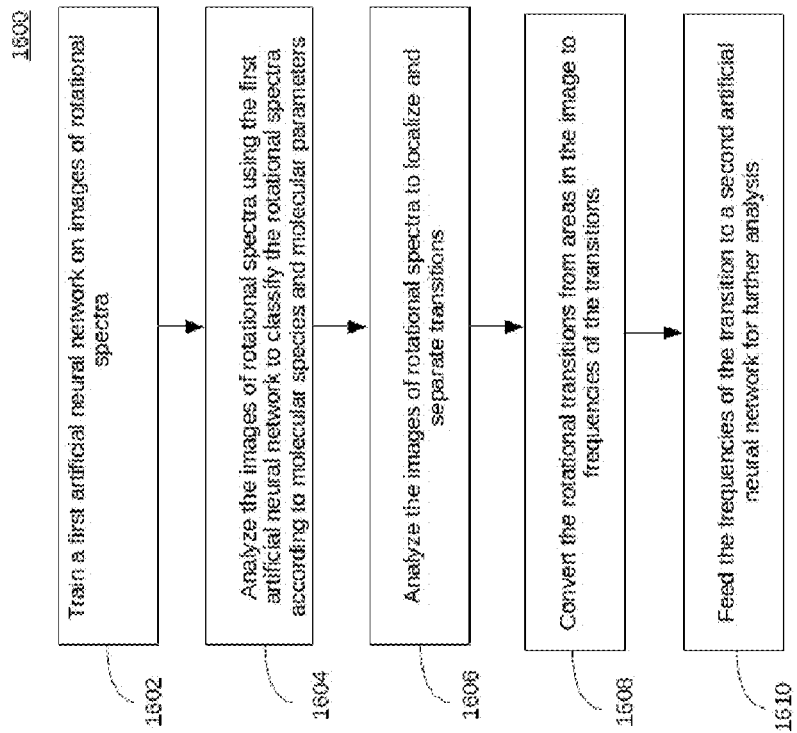
FIG. 16 depicts an exemplary method of training an artificial neural network to classify rotational spectra.

FIG. 16 depicts a method 1600 of training an artificial neural network to classify rotational spectra. The method 1600 may include training a first artificial neural network on images of rotational spectra (block 1602). The method 1600 may include analyzing the images of rotational spectra using the first artificial neural network to classify the rotational spectra according to molecular species and molecular parameters (block 1604). The method 1600 may include analyzing the images of rotational spectra using the first artificial neural network to localize rotational transitions and separate those transitions from noise, spurious lines, and other unwanted signals (block 1606). The method 1600 may include converting the rotational transitions from areas in the image to frequencies of the transitions (block 1608). The method 1600 may include feeding the frequencies of the transition to a second artificial neural network for further analysis (block 1610).

Embodiments of the techniques described in the present disclosure may include any number of the following aspects, either alone or combination:

1. A computer-implemented method of identifying molecular parameters in a complex mixture, the method comprising: receiving a set of combined transition frequencies or an image of a spectrum corresponding to the complex mixture, analyzing the set of combined transition frequencies or the image using a first trained artificial neural network to generate a plurality of separated transition frequency sets, and for each set of separated transition frequencies in the plurality of separated transition frequency sets, analyzing the set of separated transition frequencies using a second trained artificial neural network to generate a set of estimated spectral parameters; and identifying a set of molecular parameters corresponding to the set of separated transition frequencies, a set of molecular geometries corresponding to the set of separated transition frequencies, and/or a set of chemical species corresponding to the set of separated transition frequencies.

2. The computer-implemented method of claim 1, wherein receiving the set of combined transition frequencies corresponding to the complex mixture includes receiving the set of combined transition frequencies from a rotational spectrometer.

3. The computer-implemented method of claim 1, wherein the first trained artificial neural network is a convolutional neural network.

4. The computer-implemented method of claim 1, wherein the first trained artificial neural network is a recurrent neural network.

5. The computer-implemented method of claim 4, wherein the recurrent neural network includes one or more long short-term memory layers.

6. The computer-implemented method of claim 1, wherein the first trained artificial neural network is trained by analyzing a data set including one or more pair of combined spectra and separated spectra.

7. The computer-implemented method of claim 1, further comprising:
generating a visual plot of at least one of (a) the plurality of separated transition frequency sets, (b) the set of estimated spectral parameters, or (c) the set of molecular parameters.

8. The computer-implemented method of claim 7, wherein generating a visual plot includes generating a color coding.

9. The computer-implemented method of claim 1, wherein identifying a set of molecular parameters corresponding to the set of separated transition frequencies includes identifying a set of molecular parameters corresponding to the set of estimated spectral parameters.

10. A complex mixture molecular parameter identification system, comprising: a sensor capable of measuring a sample to produce a set of combined transition frequencies corresponding to the complex mixture, a user interface via which a user may interact with the complex mixture molecular parameter identification system, one or more processors; and a spectrum analysis application comprising a set of computer-executable instructions stored on one or more memories, wherein the set of computer-executable instructions, when executed by the one or more processors, cause the complex mixture molecular parameter identification system to: (i) retrieve, from the sensor, a set of combined transition frequencies, and (ii) analyze the set of combined transition frequencies to generate a set of disentangled sets of transition frequencies by analyzing the set of combined transition frequencies using a first trained artificial neural network.

11. The complex mixture molecular parameter identification system of claim 10, wherein the spectrum analysis application includes further instructions that, when executed by the one or more processors, cause the complex mixture molecular parameter identification system to: identify a Hamiltonian type corresponding to at least one of the set of disentangled sets of transition frequencies using a second artificial neural network, select, based on the identified Hamiltonian type, a third trained artificial neural network, and generate a set of molecular parameters by analyzing the at least one of the set of disentangled sets of transition frequencies using the third trained artificial neural network.

12. The complex mixture molecular parameter identification system of claim 10, wherein the sensor composes at least one of (i) a microwave rotational spectrometer, (ii) a millimeter-wave rotational spectrometer, (iii) a terahertz rotational spectrometer, or (iv) another spectrometer capable of obtaining a rotational or rotationally resolved spectrum.

13. The complex mixture molecular parameter identification system of claim 10, wherein the first trained artificial neural network is a convolutional neural network.

14. The complex mixture molecular parameter identification system of claim 10, wherein the first trained artificial neural network is a recurrent neural network.

15. The complex mixture molecular parameter identification system of claim 14, wherein the recurrent neural network includes one or more long short-term memory layers.

16. The complex mixture molecular parameter identification system of claim 10, wherein the second trained artificial neural network is a classification artificial neural network and the third artificial neural network is a regression artificial neural network.

17. The complex mixture molecular parameter identification system of claim 10, wherein the set of computer-executable instructions, when executed by the one or more processors, further cause the molecular parameter identification system to: display, in the user interface, a plot of one or both of (i) the estimated spectral parameters, and (ii) the set of molecular parameters.

18. The complex mixture molecular parameter identification system of claim 16, wherein the plot of one or both of the estimated spectral parameters and the set of molecular parameters is color-coded.

19. A non-transitory computer readable medium containing program instructions that when executed, cause a computer to: receive a set of combined transition frequencies corresponding to a complex mixture, analyze the set of combined transition frequencies using a first trained artificial neural network to generate a plurality of separated transition frequency sets, and for each set of separated transition frequencies in the plurality of separated transition frequency sets, analyze the set of separated transition frequencies using a second trained artificial neural network to generate a set of estimated spectral parameters, and based on the set of estimated spectral parameters, identify a set of molecular parameters corresponding to the set of separated transition frequencies.

20. The non-transitory computer-readable medium of claim 19 including further program instructions that when executed, cause a computer to: generate a visual plot of at least one of (a) the plurality of separated transition frequency sets, (b) the set of estimated spectral parameters, or (c) the set of molecular parameters.

21. A computer-implemented method, the method comprising: receiving a set of observed transition frequencies or an image of a spectrum, analyzing, using a trained artificial neural network, the set of observed transition frequencies or the image to predict a set of estimated spectral parameters, obtaining a set of hypothetical molecular structures, comparing the set of estimated spectral parameters to the set of hypothetical molecular structures to find a match, and identifying, based on the match, one or both of 1) a molecular geometry corresponding to the estimated spectral parameters, and 2) a chemical species corresponding to the estimated spectral parameters.

22. The computer-implemented method of claim 20, wherein obtaining the set of hypothetical molecular structures includes selecting the set of hypothetical or actual molecular structures from a database.

23. The computer-implemented method of claim 20, wherein obtaining the set of hypothetical molecular structures includes sampling the physically and chemically feasible space of such parameters as number of atoms, atomic weights, bond lengths, angles and topology, valence, molecular orbitals structure, and positions of functional groups.

24. The computer-implemented method of claim 22, wherein an artificial neural network is trained to generate molecular geometries from a large set of feasible and infeasible geometries training data.

25. A computer-implemented method, the method comprising
generating, by analyzing a set of molecular geometries, a set of rotational spectra, the set of rotational spectra corresponding, by the rules of quantum mechanics, to the set of molecular geometries, training an artificial neural network by analyzing the set of rotational spectra and the corresponding set of molecular geometries.

26. The computer-implemented method of claim 24, wherein an artificial neural network is trained to generate molecular geometries from a large set of feasible and infeasible geometries training data.

27. The computer-implemented method of claim 24, further comprising: identifying, by the trained artificial network, one or both of 1) a molecular geometry and 2) a molecular species.

28. A computer-implemented method, the method comprising training a first artificial neural network on images of rotational spectra, analyzing the images of rotational spectra using the first artificial neural network to classify the rotational spectra according to molecular species and molecular parameters, analyzing the images of rotational spectra using the first artificial neural network to localize rotational transitions and separate those transitions from noise, spurious lines, and other unwanted signals, converting the rotational transitions from areas in the image to frequencies of the transitions; and feeding the frequencies of the transition to a second artificial neural network for further analysis.

29. The computer-implemented method of claim 27, wherein the first artificial neural network is a convolutional neural network.

ADDITIONAL CONSIDERATIONS

The foregoing describes methods and systems of identifying and assigning molecules using ANNs, based on analyzing rotational spectroscopy information. However, it should be appreciated that the techniques disclosed herein are applicable not only to rotational spectra, but also to any rotationally resolved spectrum such as rotationally resolved infrared data, rotationally resolved electronic data, and data outside the microwave region of the electromagnetic spectrum. Such other rotationally resolved spectrum may include additional applications of convolutional neural networks and/or recurrent neural networks that differ from those discussed herein. In some embodiments, determining hypothetical geometries may include Bayesian methods or other statistical methods. The sources of complex and/or entangled data used in some embodiments may differ from the data produced by rotational spectroscopy machines; however the disentanglement principles disclosed herein may be readily applicable to such data.

Furthermore, the methods and systems described herein may be used in conjunction with additional and/or alternate forms of spectroscopy including, without limitation: millimeter-wave spectroscopy and terahertz spectroscopy. Similarly, millimeter-wave spectrometers and terahertz spectrometers may be used in addition to and/or instead of microwave spectrometers. Rotational spectroscopy may include any type of rotationally resolved spectroscopy including, without limitation, ro-vibrational (IR) spectroscopy. A ro-vibrational spectrometer may be used in conjunction with and/or instead of a rotational spectrometer, in some embodiments. In an embodiment, an infrared rotationally resolved spectrometer such as an IR frequency comb spectrometer may be used.

With the foregoing, users whose data is being collected and/or utilized may first opt-in. After a user provides affirmative consent, data may be collected from the user's device (e.g., a mobile computing device). In other embodiments, deployment and use of neural network models at a client or user device (e.g., the client 102 of FIG. 1) may have the benefit of removing any concerns of privacy or anonymity, by removing the need to send any personal or private data to a remote server (e.g., the server 104 of FIG. 1).

The following additional considerations apply to the foregoing discussion. Throughout this specification, plural instances may implement operations or structures described as a single instance. Although individual operations of one or more methods are illustrated and described as separate operations, one or more of the individual operations may be performed concurrently, and nothing requires that the operations be performed in the order illustrated. These and other variations, modifications, additions, and improvements fall within the scope of the subject matter herein.

The patent claims at the end of this patent application are not intended to be construed under 35 U.S.C. § 112(f) unless traditional means-plus-function language is expressly recited, such as "means for" or "step for" language being explicitly recited in the claim(s). The systems and methods described herein are directed to an improvement to computer functionality, and improve the functioning of conventional computers.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present). Herein, the term "set" may refer to any collection, list, bucket, etc. of items (including other sets) of one or more repeating or non-repeating items, whether sorted or not.

In addition, use of the "a" or "an" are employed to describe elements and components of the embodiments herein. This is done merely for convenience and to give a general sense of the description. This description, and the claims that follow, should be read to include one or at least one and the singular also includes the plural unless it is obvious that it is meant otherwise.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a machine-readable medium) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory product to which it is communicatively coupled. A further hardware module may then, at a later time, access the memory product to retrieve and process the stored output. Hardware modules may also initiate communications with input or output products, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location (e.g., within a building environment, an office environment or as a server farm), while in other embodiments the processors may be distributed across a number of locations.

The performance of certain of the operations may be distributed among the one or more processors, not only residing within a single machine, but deployed across a number of machines. In some example embodiments, the one or more processors or processor-implemented modules may be located in a single geographic location (e.g., within a building environment, an office environment, or a server farm). In other example embodiments, the one or more processors or processor-implemented modules may be distributed across a number of geographic locations.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

Upon reading this disclosure, those of skill in the art will appreciate still additional alternative structural and functional designs for the method and systems described herein through the principles disclosed herein. Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

What is claimed:

1. A computer-implemented method of identifying molecular parameters in a gas phase mixture including one or more molecules, the method comprising:
receiving a set of combined transition frequencies or an image of a spectrum corresponding to the mixture,
analyzing the set of combined transition frequencies or the image using a first trained artificial neural network to generate a plurality of separated transition frequency sets, and
for each set of separated transition frequencies in the plurality of separated transition frequency sets,
analyzing the set of separated transition frequencies using a second trained artificial neural network to generate a set of estimated spectral parameters; and
identifying a set of molecular parameters corresponding to the set of separated transition frequencies, a set of molecular geometries corresponding to the set of separated transition frequencies, and/or a set of chemical species corresponding to the set of separated transition frequencies.

2. The computer-implemented method of claim 1, wherein receiving the set of combined transition frequencies corresponding to the mixture includes receiving the set of combined transition frequencies from a rotational spectrometer.

3. The computer-implemented method of claim 1, wherein the first trained artificial neural network is a convolutional neural network.

4. The computer-implemented method of claim 1, wherein the first trained artificial neural network is a recurrent neural network.

5. The computer-implemented method of claim 4, wherein the recurrent neural network includes one or more long short-term memory layers.

6. The computer-implemented method of claim 1, wherein the first trained artificial neural network is trained by analyzing a data set including one or more pair of combined spectra and separated spectra.

7. The computer-implemented method of claim 1, further comprising:
generating a visual plot of at least one of (a) the plurality of separated transition frequency sets, (b) the set of estimated spectral parameters, or (c) the set of molecular parameters.

8. The computer-implemented method of claim 7, wherein generating a visual plot includes generating a color coding.

9. The computer-implemented method of claim 1, wherein identifying a set of molecular parameters corresponding to the set of separated transition frequencies includes identifying a set of molecular parameters corresponding to the set of estimated spectral parameters.

10. A gas phase mixture molecular parameter identification system, comprising:
a sensor capable of measuring a sample including one or more molecules to produce a set of combined transition frequencies corresponding to the mixture,
a user interface via which a user may interact with the mixture molecular parameter identification system,
one or more processors; and
a spectrum analysis application comprising a set of computer-executable instructions stored on one or more memories, wherein the set of computer-executable instructions, when executed by the one or more processors, cause the mixture molecular parameter identification system to:
(i) retrieve, from the sensor, a set of combined transition frequencies, and
(ii) analyze the set of combined transition frequencies to generate a set of disentangled sets of transition frequencies by analyzing the set of combined transition frequencies using a first trained artificial neural network.

11. The mixture molecular parameter identification system of claim 10, wherein the spectrum analysis application includes further instructions that, when executed by the one or more processors, cause the mixture molecular parameter identification system to:
identify a Hamiltonian type corresponding to at least one of the set of disentangled sets of transition frequencies using a second artificial neural network,
select, based on the identified Hamiltonian type, a third trained artificial neural network, and
generate a set of molecular parameters by analyzing the at least one of the set of disentangled sets of transition frequencies using the third trained artificial neural network.

12. The mixture molecular parameter identification system of claim 10, wherein the sensor composes at least one of (i) a microwave rotational spectrometer, (ii) a millimeter-wave rotational spectrometer, (iii) a terahertz rotational spectrometer, or (iv) another spectrometer capable of obtaining a rotational or rotationally resolved spectrum.

13. The mixture molecular parameter identification system of claim 10, wherein the first trained artificial neural network is a convolutional neural network.

14. The mixture molecular parameter identification system of claim 10, wherein the first trained artificial neural network is a recurrent neural network.

15. The mixture molecular parameter identification system of claim 14, wherein the recurrent neural network includes one or more long short-term memory layers.

16. The mixture molecular parameter identification system of claim 10, wherein the second trained artificial neural network is a classification artificial neural network and the third artificial neural network is a regression artificial neural network.

17. The mixture molecular parameter identification system of claim 10, wherein the set of computer-executable instructions, when executed by the one or more processors, further cause the molecular parameter identification system to:
display, in the user interface, a plot of one or both of (i) the estimated spectral parameters, and (ii) the set of molecular parameters.

18. The mixture molecular parameter identification system of claim 16, wherein the plot of one or both of the estimated spectral parameters and the set of molecular parameters is color-coded.

19. A non-transitory computer readable medium containing program instructions that when executed, cause a computer to:
receive a set of combined transition frequencies corresponding to a gas phase mixture including one or more molecules,
analyze the set of combined transition frequencies using a first trained artificial neural network to generate a plurality of separated transition frequency sets, and
for each set of separated transition frequencies in the plurality of separated transition frequency sets,
analyze the set of separated transition frequencies using a second trained artificial neural network to generate a set of estimated spectral parameters, and based on the set of estimated spectral parameters, identify a set of molecular parameters corresponding to the set of separated transition frequencies.

20. The non-transitory computer-readable medium of claim 19 including further program instructions that when executed, cause a computer to:
generate a visual plot of at least one of (a) the plurality of separated transition frequency sets, (b) the set of estimated spectral parameters, or (c) the set of molecular parameters.

* * * * *